US011446046B2

(12) United States Patent
Nelson et al.

(10) Patent No.: US 11,446,046 B2
(45) Date of Patent: Sep. 20, 2022

(54) TOOL EXCHANGE SYSTEM FOR A SURGICAL ROBOT

(71) Applicant: NUtech Ventures, Lincoln, NE (US)

(72) Inventors: Carl A. Nelson, Lincoln, NE (US); Raul Gonzalo Garay Romero, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 473 days.

(21) Appl. No.: 16/113,686

(22) Filed: Aug. 27, 2018

(65) Prior Publication Data

US 2020/0060774 A1  Feb. 27, 2020

Related U.S. Application Data

(60) Provisional application No. 62/550,622, filed on Aug. 26, 2017.

(51) Int. Cl.
| | |
|---|---|
| *A61B 17/29* | (2006.01) |
| *A61B 34/30* | (2016.01) |
| *A61B 17/34* | (2006.01) |
| *A61B 18/14* | (2006.01) |

(52) U.S. Cl.
CPC .......... *A61B 17/29* (2013.01); *A61B 17/3421* (2013.01); *A61B 18/1442* (2013.01); *A61B 34/30* (2016.02); *A61B 2017/2901* (2013.01); *A61B 2017/2927* (2013.01); *A61B 2034/302* (2016.02)

(58) Field of Classification Search
CPC . A61B 17/29; A61B 17/3421; A61B 18/1442; A61B 2034/302; A61B 2017/2901; A61B 2017/2927; A61B 2017/2926; A61B 34/30
See application file for complete search history.

(56) References Cited

U.S. PATENT DOCUMENTS

| 5,331,971 | A | * | 7/1994 | Bales | A61B 10/06 600/564 |
|---|---|---|---|---|---|
| 5,374,277 | A | * | 12/1994 | Hassler | A61B 17/29 606/170 |
| 5,893,875 | A | * | 4/1999 | O'Connor | A61B 17/29 606/205 |
| 2002/0040217 | A1 | * | 4/2002 | Jinno | B25J 3/04 606/1 |
| 2003/0191494 | A1 | * | 10/2003 | Gray | A61B 17/122 606/205 |
| 2004/0133235 | A1 | * | 7/2004 | Bacher | A61B 17/29 606/205 |

(Continued)

*Primary Examiner* — Jing Rui Ou
(74) *Attorney, Agent, or Firm* — Leydig, Voit & Mayer, Ltd.

(57) ABSTRACT

A surgical tool exchanger includes an elongated base having a first end and a second end. The surgical tool exchanger also includes an end effector configured to receive a replaceable surgical tool and an elbow configured to allow the end effector to pivot with respect to the elongated base. The surgical tool exchanger further includes an actuator connected to the second end of the elongated base. The actuator is operatively connected to the end effector and is configured to cause the end effector to retain the replaceable surgical tool in a first actuation state and release the replaceable surgical tool in a second actuation state.

7 Claims, 22 Drawing Sheets

(56) References Cited

U.S. PATENT DOCUMENTS

| | | | |
|---|---|---|---|
| 2007/0233052 A1* | 10/2007 | Brock | A61B 34/30 606/1 |
| 2009/0320637 A1* | 12/2009 | Doyle | A61B 34/70 74/490.03 |
| 2011/0087265 A1* | 4/2011 | Nobis | A61B 17/29 606/205 |
| 2012/0109186 A1* | 5/2012 | Parrott | A61B 17/2909 606/206 |

\* cited by examiner

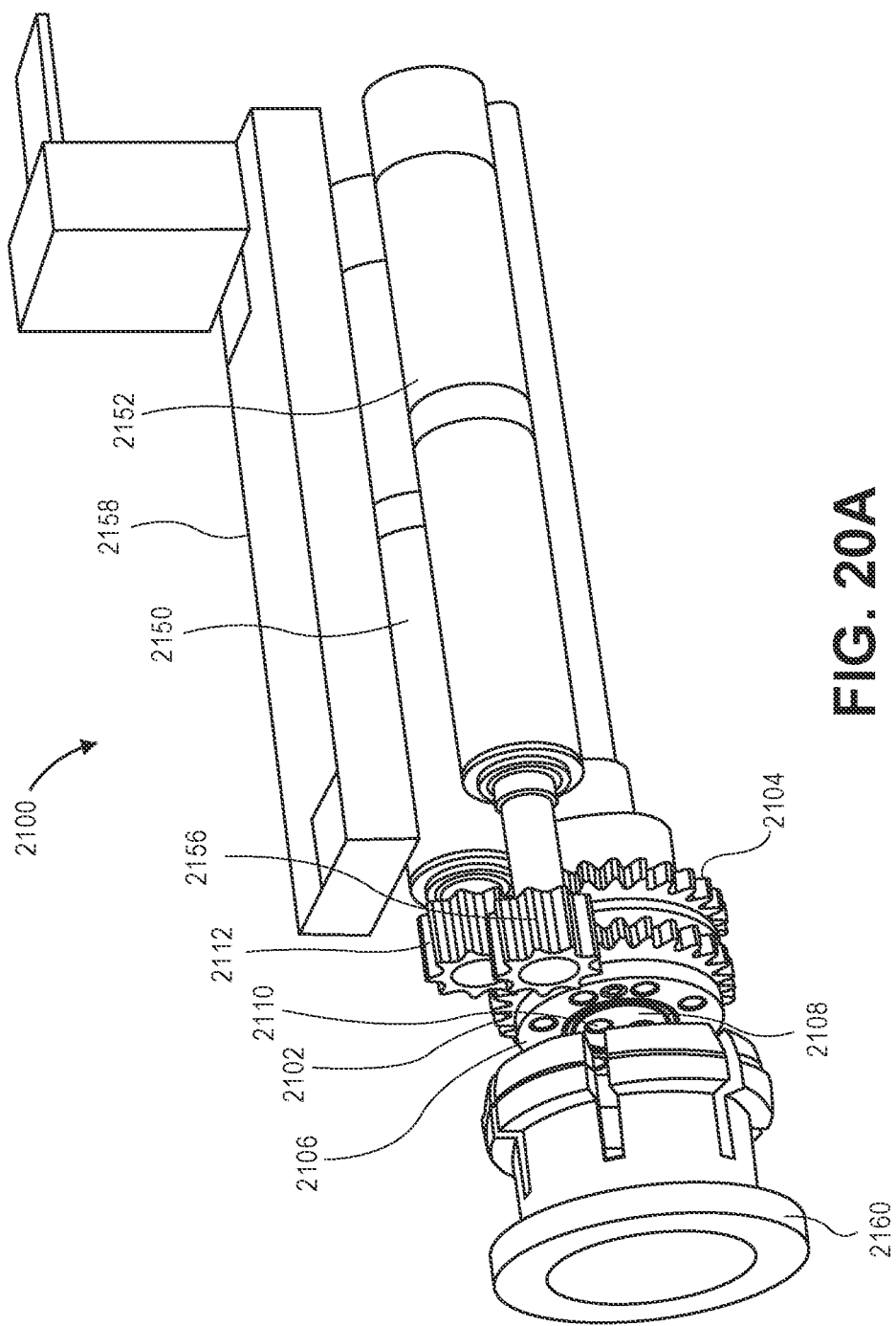

TOOL EXCHANGE SYSTEM FOR A SURGICAL ROBOT

CROSS-REFERENCE TO RELATED APPLICATIONS

This application claims the benefit of U.S. Provisional Application No. 62/550,622, filed Aug. 26, 2017. The entire disclosure of the application referenced above is incorporated by reference.

STATEMENT REGARDING FEDERALLY SPONSORED RESEARCH OR DEVELOPMENT

This invention was made with government support under W81XWH-14-1-0058 awarded by the Department of Defense, US Army Medical Research and Material Command. The government has certain rights in the invention.

FIELD

The present disclosure relates to surgical devices, and more specifically to a tool exchange system for surgical devices.

BACKGROUND

Medical professionals typically employ laparoscopes to perform minimally invasive surgery on a patient's abdominal cavity for diagnostic and treatment purposes. Generally, laparoscopes comprise an instrument configured to pass through a small incision and capture images of areas within a patient. During use, laparoscopes require multiple types of equipment, such as power sources, insufflators and so on, which are coupled to the laparoscope via a wiring/tube harness.

Laparoscopes are used to perform minimally invasive surgeries. During a medical procedure, an incision is created to allow a surgical tool to enter the patient's body. A trocar may be inserted in the incision, and the trocar functions as a portal allowing the insertion of the surgical tools. Multiple surgical tools may be used during the operation, which may require the laparoscope to be removed and inserted through the incision multiple times to allow exchanging of the surgical tools.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A surgical tool exchanger includes an elongated base having a first end and a second end, an end effector configured to receive a replaceable surgical tool, and an elbow configured to allow the end effector to pivot with respect to the elongated base. The surgical tool exchanger also includes an actuator connected to the second end of the elongated base and operatively connected to the end effector. The actuator is configured to cause the end effector to retain the replaceable surgical tool in a first actuation state and release the replaceable surgical tool in a second actuation state.

In other features, the end effector includes a body and a plurality of jaws connected to the body. In the first actuation state, the actuator causes the plurality of jaws to grip the replaceable surgical tool. In the second actuation state, the actuator causes the plurality of jaws to release the replaceable surgical tool.

In further features, the surgical tool exchanger includes an overtube that is configured to slide from a first position to a second position over the body. Movement of the overtube to the first position biases the plurality of jaws in a grasping state. Movement of the overtube to the second position causes the plurality of jaws to transition to a non-grasping state.

In yet further features, the end effector comprises a biasing member that biases the overtube toward the first position.

In other features, in the first actuation state, the actuator allows the overtube to move to the first position and in the second actuation state, the actuator moves the overtube to the second position. The overtube is configured to, in the first position, press on a collet retaining a shaft of the replaceable surgical tool in a surgical robot.

In other features, the biasing member is a coil spring.

In yet other features, the surgical tool exchanger includes a cable connected between the actuator and the end effector. In response to the actuator applying tension to the cable, the cable moves the overtube toward the second position.

In other features, the plurality of jaws are biased to pivot away from a central axis of the overtube. In further features, each jaw of the plurality of jaws is attached to spring steel that presses the jaw away from the central axis of the overtube.

In other features, each jaw of the plurality of jaws includes a protrusion to engage an annular barb of the replaceable surgical tool. The annular barb is symmetric about an axis that, when the replaceable surgical tool is retained by the end effector, is collinear with a central axis of the body.

In yet other features, each jaw of the plurality of jaws includes a plurality of protrusions to respectively engage a plurality of annular barbs of the replaceable surgical tool. Each barb of the plurality of annular barbs is symmetric about an axis that, when the replaceable surgical tool is retained by the end effector, is collinear with a central axis of the body.

In other features, the plurality of jaws are connected to a carrier that is rotatably connected to the body. Each jaw of the plurality of jaws includes a protrusion that engages a recess in the replaceable surgical tool. Rotation of the carrier causes a first face of the protrusion to bear on a second face of the recess. The first and second faces are parallel to an axis of rotation of the carrier.

In further features, the surgical tool exchanger includes a first rod within the elongated base and a joint located within the elbow. The joint transfers rotational motion of the first rod to the carrier. In yet further features, the joint includes a universal joint.

In other features, the end effector includes a first beam holding a first jaw of the plurality of jaws and extending outwardly from the body and a second beam holding a second jaw of the plurality of jaws and extending outwardly from the body. The end effector further includes a slider configured to slide within a cavity defined in the body between a first position and a second position, a first end-effector actuator connected to the second jaw and the slider, and a second end-effector actuator connected to the first jaw and the slider. In the first actuation state, the actuator causes the slider to move to the first position. In the second actuation state, the actuator causes the slider to move to the second position.

In further features, the first end effector actuator includes a first cable configured to be pulled by the slider. The second end effector actuator includes a second cable configured to be pulled by the slider.

In other features, the first end effector actuator and the second end effector actuator are arranged in a crisscross configuration.

In other features, the surgical tool exchanger includes a first rod within the elongated base, a second rod within the end effector, and a joint located within the elbow. The joint transfers rotational motion of the first rod to the second rod.

A surgical tool exchanger includes an elongated base having a first end and a second end and an end effector connected to the elongated base and configured to receive a replaceable surgical tool. The surgical tool exchanger also includes an actuator connected to the second end of the elongated base and operatively connected to the end effector and configured to cause the end effector to retain the replaceable surgical tool in a first actuation state and release the replaceable surgical tool in a second actuation state. The end effector includes a body and a plurality of jaws connected to the body. In the first actuation state, the actuator causes the plurality of jaws to grip the replaceable surgical tool. In the second actuation state, the actuator causes the plurality of jaws to release the replaceable surgical tool. The end effector further includes an overtube that is configured to slide from a first position to a second position over the body and a biasing member that biases the overtube toward the first position. Movement of the overtube to the first position biases the plurality of jaws in a grasping state. Movement of the overtube to the second position causes the plurality of jaws to transition to a non-grasping state.

A surgical tool exchanger includes an elongated base having a first end and a second end. The surgical tool-exchanger also includes an end effector connected to the elongated base and configured to receive a replaceable surgical tool and an actuator connected to the second end of the elongated base and operatively connected to the end effector and configured to cause the end effector to retain the replaceable surgical tool in a first actuation state and release the replaceable surgical tool in a second actuation state. The end effector includes a body and a plurality of jaws connected to the body. In the first actuation state, the actuator causes the plurality of jaws to grip the replaceable surgical tool. In the second actuation state, the actuator causes the plurality of jaws to release the replaceable surgical tool. The end effector further includes a first beam holding a first jaw of the plurality of jaws and extending outwardly from the body, a second beam holding a second jaw of the plurality of jaws and extending outwardly from the body, a slider configured to slide within a cavity defined in the body between a first position and a second position, a first end effector actuator connected to the second jaw and the slider, and a second end effector actuator connected to the first jaw and the slider. In the first actuation state, the actuator causes the slider to move to the first position. In the second actuation state, the actuator causes the slider to move to the second position.

A robotic arm for a surgical robot, the robotic arm includes a first rotary engagement mechanism configured to (i) removably engage a housing of a replaceable surgical tool and (ii) selectively rotate the housing and a second rotary engagement mechanism configured to (i) removably engage an inner member of the replaceable surgical tool and (ii) selectively rotate the inner member with respect to the housing. A rotation face of the first rotary engagement mechanism is coplanar with an actuation face of the second rotary engagement mechanism. The robotic arm also includes a plurality of electrical contacts configured to transmit electrical power to the replaceable surgical tool and a retention member configured to selectively press an end of the replaceable surgical tool against the rotation face and the actuation face.

In further features, the robotic arm includes a first motor configured to drive the first rotary engagement mechanism. In other features, the robotic arm includes a ring gear directly coupled to the first rotary engagement mechanism. The ring gear meshes with a pinion gear driven by the first motor.

In yet other features, the robotic arm includes a second motor configured to drive the second rotary engagement mechanism. In further features, the robotic arm includes a ring gear directly coupled to the second rotary engagement mechanism. The ring gear meshes with a pinion gear driven by the second motor.

In other features, the retention member includes a releasable push fitting. The releasable push fitting includes a movable collet and a grab ring. The collet presses the grab ring against a cylindrical portion of the replaceable surgical tool.

In further features, the collet is moved to decrease friction between the grab ring and the cylindrical portion to remove the replaceable surgical tool from the retention member.

In other features, the retention member includes a twist-to-lock fitting.

In yet other features, the actuation face includes a plurality of pockets configured to receive a respective plurality of pins of the inner member of the replaceable surgical tool.

In further features, a first pocket of the plurality of pockets includes a conductive material to electrically interface with the respective pin of the plurality of pins and a second pocket of the plurality of pockets includes a conductive material to electrically interface with the respective pin of the plurality of pins. The first pocket is electrically isolated from the second pocket.

In other features, the rotation face includes a plurality of pockets configured to receive a respective plurality of pins of the housing of the replaceable surgical tool.

A replaceable surgical tool for a surgical robot, the replaceable surgical tool includes a housing that includes a first face and an inner member that rotates within the housing about a central axis of the housing and that includes a second face. The first face and the second face are coplanar and concentric and the second face is smaller than the first face. While the replaceable surgical tool is retained by the surgical robot, (i) the first face engages a rotation face of the surgical robot, (ii) rotation of the rotation face causes rotation of the first face, (iii) the second face engages an actuation face of the surgical robot, and (iv) rotation of the actuation face causes rotation of the second face.

In further features, the second face includes a plurality of pins configured to respectively engage a plurality of pockets of the actuation face.

In other features, each pin of the plurality of pins is spring-loaded.

In yet other features, a first pin of the plurality of pins is configured to electrically connect to the respective pocket of the plurality of pockets. A second pin of the plurality of pins is configured to electrically connect to the respective pocket of the plurality of pockets. The first pin is electrically isolated from the second pin.

In further features, the inner member includes a first conductive band electrically connected to the first pin, a second conductive band electrically connected to the second pin, and an insulator band located between the first conductive band and the second conductive band. The housing includes a first conductor that engages the first conductive band at a first location. The first location changes as the inner member rotates with respect to the housing. The housing further includes a second conductor that engages the second conductive band at a second location. The second location changes as the inner member rotates with respect to the housing.

In other features, the replaceable surgical tool includes a first member pivotally coupled to the housing and a second member pivotally coupled to the housing. Rotation of the inner member with respect to the housing causes the first member and the second member to pivot with respect to each other.

In further features, the replaceable surgical tool includes a threaded member that engages threads of the inner member. The threaded member slides along an axis parallel to the central axis and rotation of the threaded member is prevented by the housing. The threaded member bears on the first member and the second member such that movement of the threaded member along the axis causes the first member and the second member to pivot with respect to each other.

In yet other features, the first face includes a plurality of pins configured to respectively engage a plurality of pockets of the rotation face. In further features, each pin of the plurality of pins is spring-loaded.

In other features, the housing includes an annular barb that is symmetric about the central axis of the housing. The annular barb remains exposed when the replaceable surgical tool is held by the surgical robot.

In yet other features, the housing includes a plurality of annular barbs that are each symmetric about the central axis of the housing. The plurality of annular barbs remain exposed when the replaceable surgical tool is held by the surgical robot.

In further features, the housing includes a plurality of elongated recesses. Each of the plurality of elongated recesses extends in a direction parallel to the central axis of the housing. The plurality of elongated recesses remains exposed when the replaceable surgical tool is held by the surgical robot.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

The present disclosure is directed to a surgical tool exchanger system that provides for exchanging of the surgical tool within the body. For example, a second incision can be made proximate to the first incision, and a second trocar can be inserted in the second incision. Medical personnel can then use a surgical tool exchanger to unmount a surgical tool connected to the surgical robot. Once unmounted from the surgical robot, the surgical tool exchanger can remove the unmounted surgical tool from the second incision. The desired surgical tool can then be attached to surgical tool exchanger, and the medical personnel can then use the surgical tool exchanger to mount the attached surgical tool to the surgical robot within the body.

Figure 1:
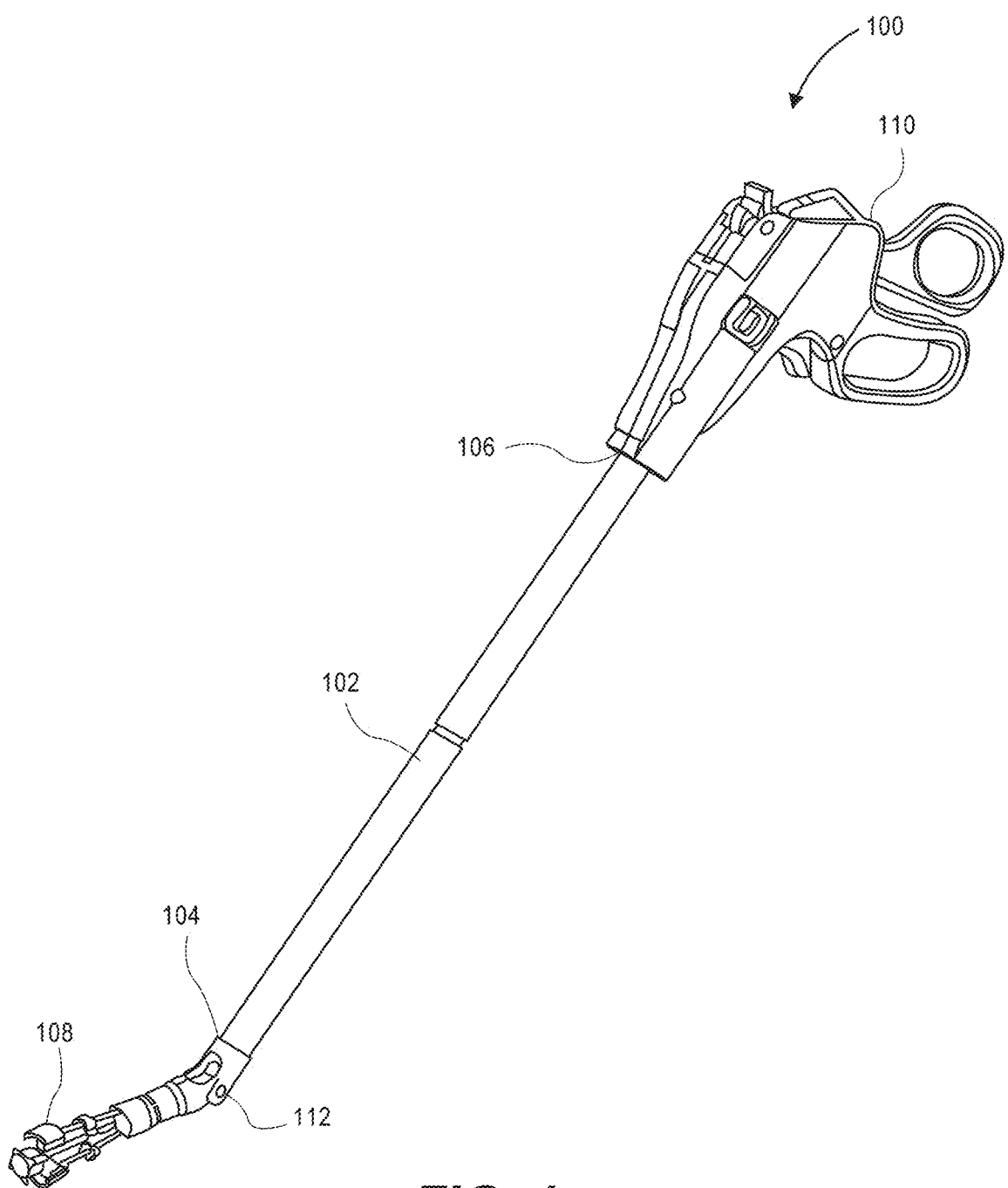
FIG. 1 is an isometric view of a surgical tool exchanger according to an example implementation of the present disclosure.

FIG. 1 illustrates an example surgical tool exchanger 100 according to an example implementation of the present disclosure. As shown, the surgical tool exchanger 100 includes an elongated base 102, such as an elongated shaft, having a first end 104 and a second end 106. The surgical tool exchanger 100 also includes an end effector 108 that is disposed proximate to the first end 104 and an actuator 110 connected to the second end 106. The actuator 110 can actuate the end effector 108 to retain a removable surgical tool in a first actuation state and release the removable surgical tool in a second actuation state.

As shown, the surgical tool exchanger 100 includes an elbow 112 that pivotally connects the elongated base 102 to the end effector 108. The elbow 112 pivots about an axis that is defined as being parallel with a top surface of the elongated base 102. The elbow 112 can pivot about the axis to allow the end effector 108 to axially align with an arm of the surgical robot.

Figure 3:
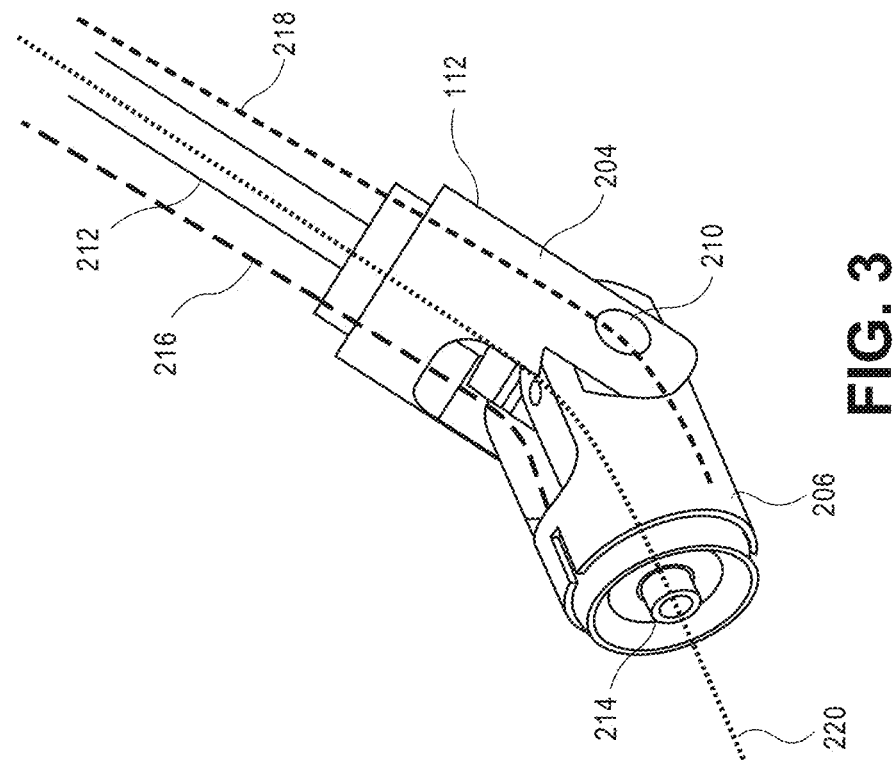
FIGS. 2 and 3 are partial isometric views of an elbow of surgical tool exchanger according to an example implementation of the present disclosure.
Figure 2:
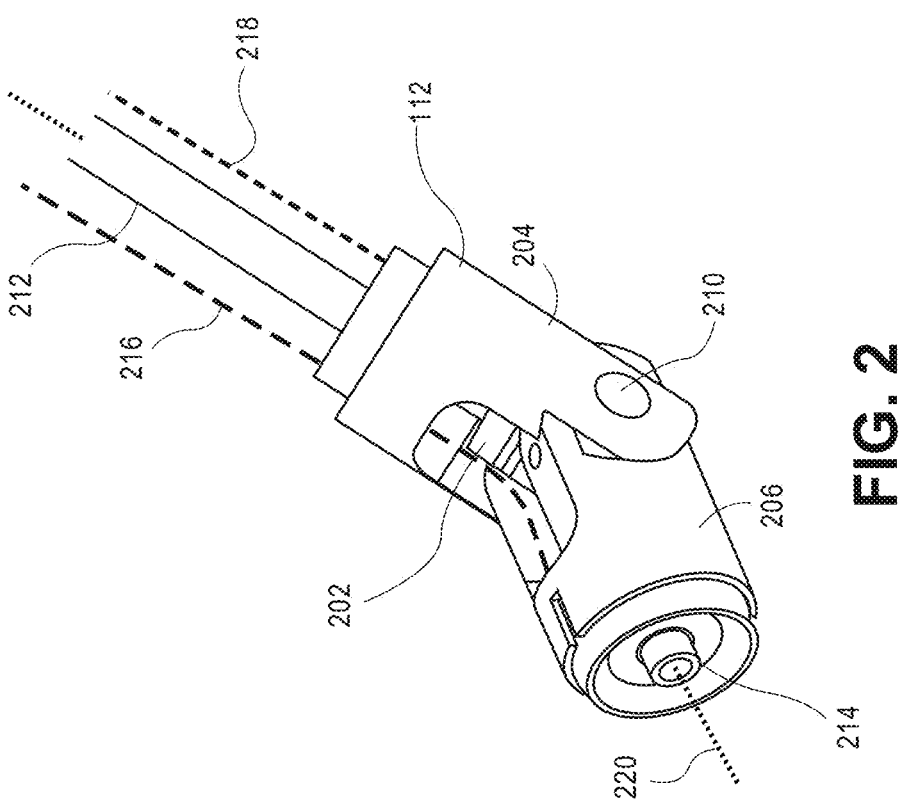

FIGS. 2 and 3 illustrate an example implementation of the elbow 112. The elbow 112 includes a joint 202 disposed within a first elbow portion 204 and a second elbow portion 206. The elbow portions 204, 206 are connected to each other via a rotational pin fastener 210 that allows the elbow portions 204, 206 to pivot relative to one another based upon the actuation of the actuator 110. In an implementation, the joint 202 comprises a universal joint. The elbow portions 204, 206 and the pin 210 are arranged to allow the joint 202 to pivot within a single plane. For example the elbow portions 204, 206 can restrict angular movement of the joint 202.

The surgical tool exchanger 100 includes end effector actuation rods 212, 214 that actuates the end effector 108. One end of the end effector actuation rod 212 is connected to the actuator 110 and the other end is connected to one end of the joint 202. One end of the end effector actuation rod 214 is connected to the other end of the joint 202 and the other end of the end effector actuation rod 214 is connected to the end effector 108. The joint 202 transfers rotational motion of the end effector actuation rod 212 to the end effector actuation rod 214.

In an implementation, the end effector actuation rod 212 is disposed within the elongated base 102 and is connected to the joint 202. For example, the elongated base 102 can define an inner cavity that retains the end effector actuation rod 212.

As shown in FIGS. 2 and 3, the surgical tool exchanger 100 also includes a first elbow actuation cable 216 and a second elbow actuation cable 218 that control movement of the elbow 112. The elbow actuation cables 216, 218 can also be disposed within the elongated base 102. For example, the elbow actuation cables 216, 218 can be disposed within the inner cavity defined by the elongated base 102. In an implementation, an end of the elbow actuation cables 216, 218 is connected to actuator 110 and the other end is connected to the second elbow portion 206.

Using the actuator 110, the elbow actuation cables 216, 218 can be independently actuated to pivot the elbow 112 in a first direction or a second direction. For example, when the actuator 110 exerts a pulling force on the first elbow actuation cable 216, the first elbow actuation cable 216 exerts a force on the second elbow portion 206 causing the second elbow portion 206 to rotate about the rotational fastener pin 210 relative to the first elbow portion 204 in a first direction. In another example, when the actuator 110 exerts a pulling force on the second elbow actuation cable 218, the second elbow actuation cable 218 exerts a force on the second elbow portion 206 causing the second elbow portion 206 to rotate about the rotational fastener pin 210 relative to the second elbow portion 206 in a second direction that is opposite the first direction.

The surgical tool exchanger 100 also includes an end effector actuation cable 220. One end of the end effector actuation cable 220 is connected to the actuator 110, and the other end of the end effector actuation cable 220 is connected to the end effector 108. The end effector actuation cable 220 can be disposed within the elongated base 102 and through the joint 202. The end effector actuation cable 220 actuates the end effector 108 between a grasping state and a non-grasping state.

Figure 4:
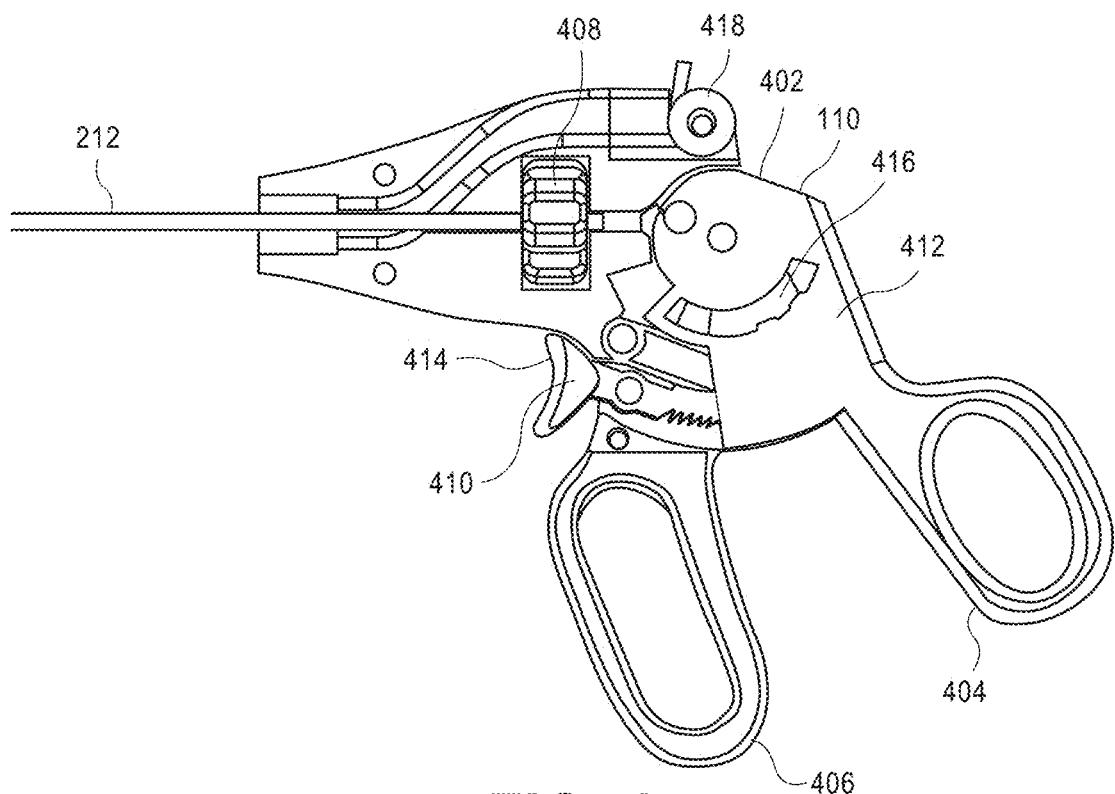
FIGS. 4 and 5 are partial isometric views of handle assembly of surgical tool exchanger according to an example implementation of the present disclosure.
Figure 5:
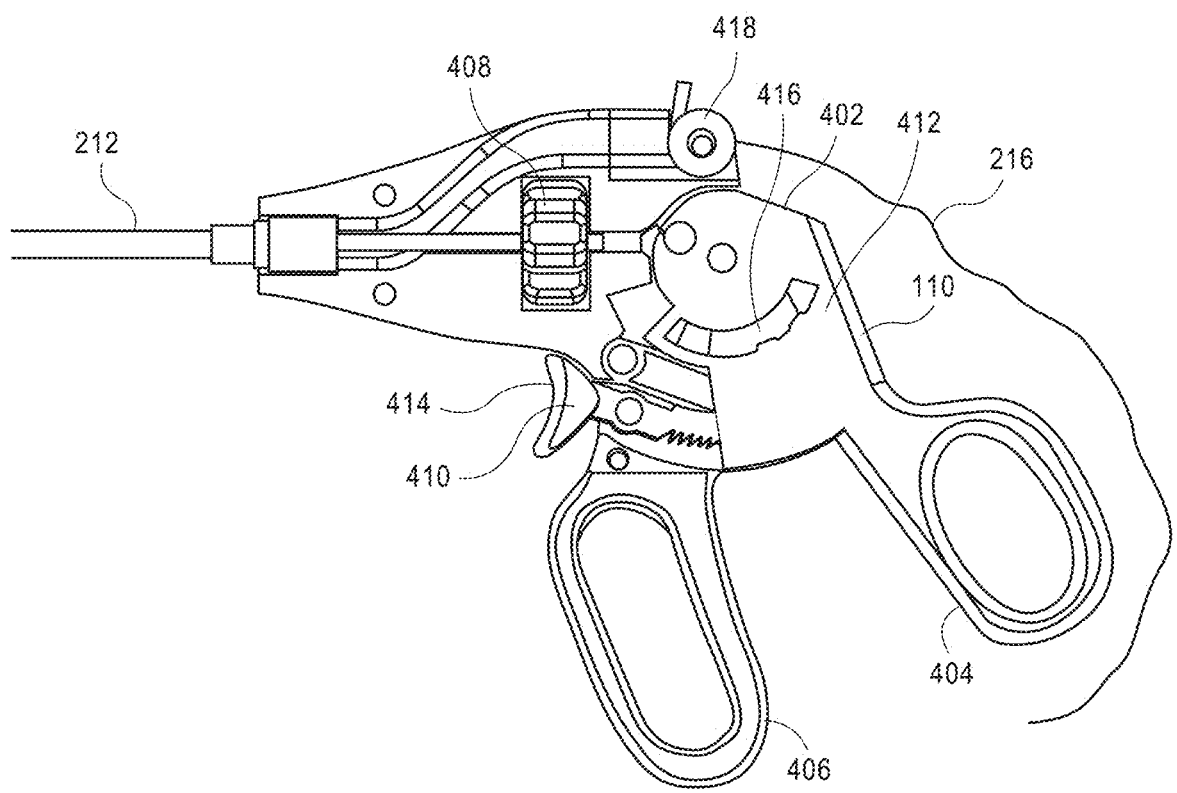

FIGS. 4 and 5 illustrate an example implementation of the actuator 110. In this implementation, the actuator 110 comprises a handle assembly 402. The handle assembly 402 includes a first handle 404, a second handle 406, a wheel 408, and a trigger 410. The handle assembly 402 includes a body 412, and the handles 404, 406 are connected to the body 412. An operator can guide the surgical tool exchanger 100 using the handles 404, 406. The wheel 408 is connected to the body 412 and can rotate about a central axis of the body 412. The wheel 408 is connected to one end of the end effector actuation rod 212. The wheel 408 transfers rotation to the end effector actuation rod 212 to rotate the end effector 108.

The trigger 410 can include a rachet and pawl mechanism 414. The rachet and pawl mechanism 414 is connected to one end of the end effector actuation cable 220. When an operator engages the rachet and pawl mechanism 414 via the trigger 410, the rachet and pawl mechanism 414 exerts a force on the end effector actuation cable 220. As described herein, the end effector actuation cable 220 actuates the end effector 108. The operator can actuate the trigger 410 to disengage the rachet and pawl mechanism 414. For example, when the trigger 410 is actuated, a biasing member 416 biases the rachet and pawl mechanism 414 to an unactuated state.

The handle mechanism 402 can include a wheel and lever mechanism 418 that controls operation of the elbow 112. For example, one end of the elbow actuation cables 216, 218 is connected to the wheel and lever mechanism 418, and the wheel and lever mechanism 418 can be actuated by the operator to actuate the elbow actuation cables 216, 218 to control movement of elbow 112.

Figure 6:
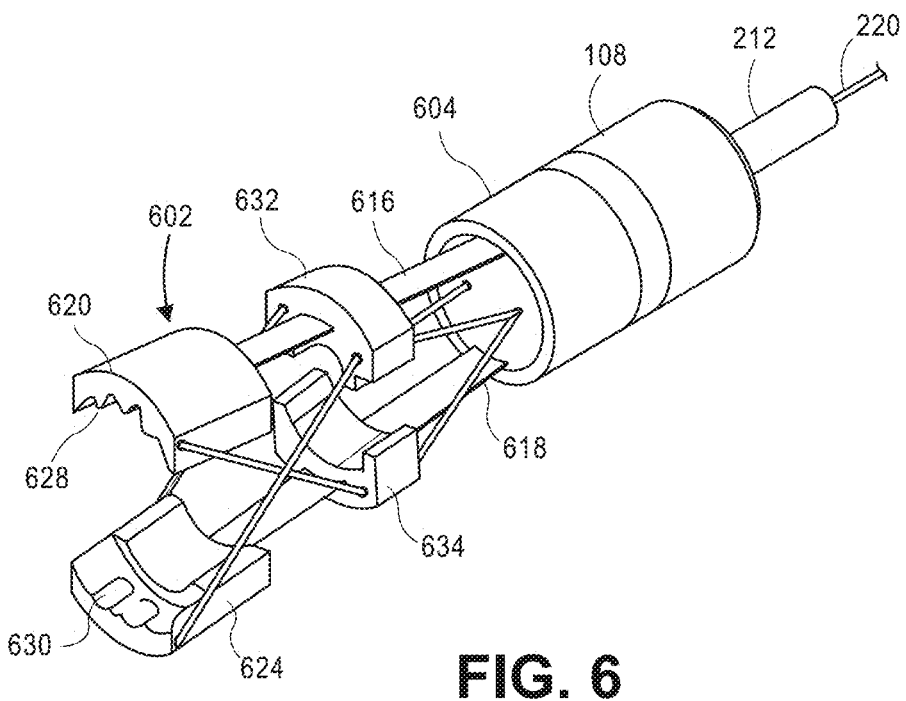
FIG. 6 is a partial isometric view of an end effector of the surgical tool exchanger according to an example implementation of the present disclosure.
Figure 7:
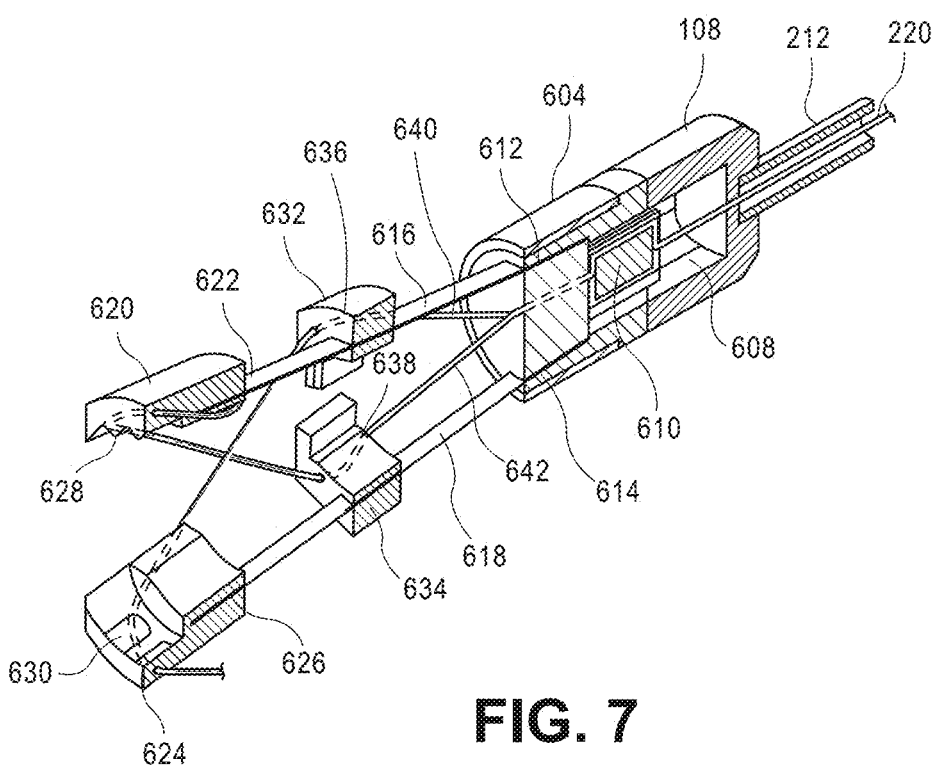
FIG. 7 is a partial isometric cross-sectional view of an end effector of the surgical tool exchanger according to an example implementation of the present disclosure.
Figure 8:
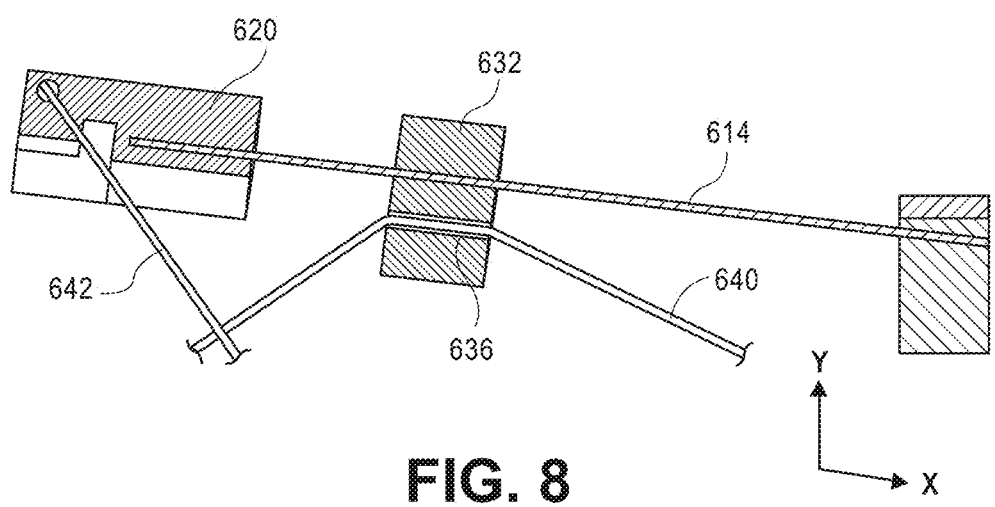
FIG. 8 a partial isometric view of the end effector of the surgical tool exchanger according to an example implementation of the present disclosure.

FIGS. 6 through 8 illustrate an example implementation of the end effector 108. In this implementation, the end effector 108 comprises a grasping device 602 that includes a base 604. The base 604 is connected to the end effector actuation rod 212 to allow the base 604 to rotate according to the actuator 110. In some instances, the end effector actuation rod 212 defines an inner cavity, and the end effector actuation cable 220 is disposed within the inner cavity.

The base 604 defines an inner cavity 608 that includes a slider 610. The slider 610 can slide between a first position and a second position within the inner cavity 608. As shown, the end effector actuation cable 220 is connected to the slider 610. When the actuator 110 exerts a pulling force on the end effector actuation cable 220, the end effector actuation cable 220 pulls the slider 610 from the first position to the second position. In some implementations, a biasing member, such as a coil spring, can be disposed within the inner cavity 608 to return the slider 610 to the first position.

The base 604 also defines a first beam receiving cavity 612 and a second beam receiving cavity 614. The beam receiving cavities 612, 614 include respective beams 616, 618 that extend outwardly from the base 604. A first outer portion 620 is disposed at an end 622 of the beam 616, and a second outer portion 624 is disposed at an end 626 of the beam 618. The outer portions 620, 624 define multiple jaws 628, 630 that mate with corresponding protrusions disposed on the surgical tool as discussed below. A first intermediate portion 632 is disposed on the beam 616, and a second intermediate portion 634 is disposed on the beam 618.

The intermediate portions 632, 634 define cable channels 636, 638 that receive actuation cables 640, 642. The actuation cables 640, 642 are connected to the slider 610 at one end and are connected to the outer portions 620, 624 at the other end.

Figure 9:
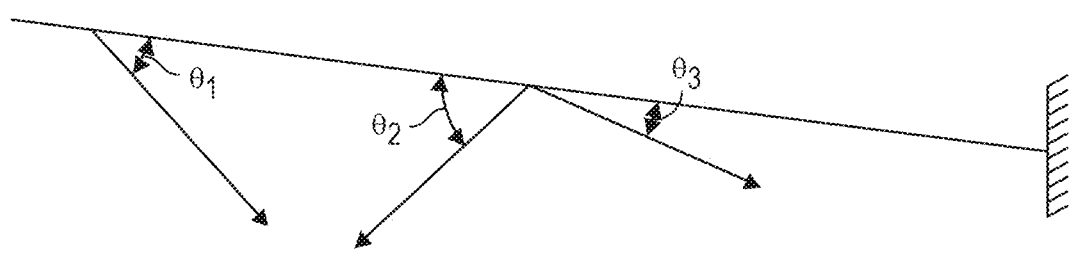
FIG. 9 is a graphical illustration of the forces exerted on a beam of the end effector according to an example implementation of the present disclosure.

The beams 616, 618 are configured to transition from a non-grasping state to a grasping state when the slider 610 slides from the first position to the second position. The beams 616, 618 are offset with respect to horizontal (see FIG. 8). Thus, when the slider 610 is slid from the first position to the second position, the slider 610 exerts a pulling force on the actuation cables 640, 642 to transition the beams 616, 618 from the non-grasping state to the grasping state. FIG. 9 illustrates that the actuation cables 640, 642 exert at least three pulling forces on the beam 616. The actuation cables 640, 642 are arranged in a crisscrossed configuration to so that the outer portions 620, 624 exert sufficient force on the surgical tool when the beams 616, 618 are in the grasping state. In an example implementation, the beams 616, 618 comprise spring steel having a Young's Modulus of at least 30,000 kilopounds per square inch (ksi) (207,000 Megapascals (MPa)).

Figure 10:
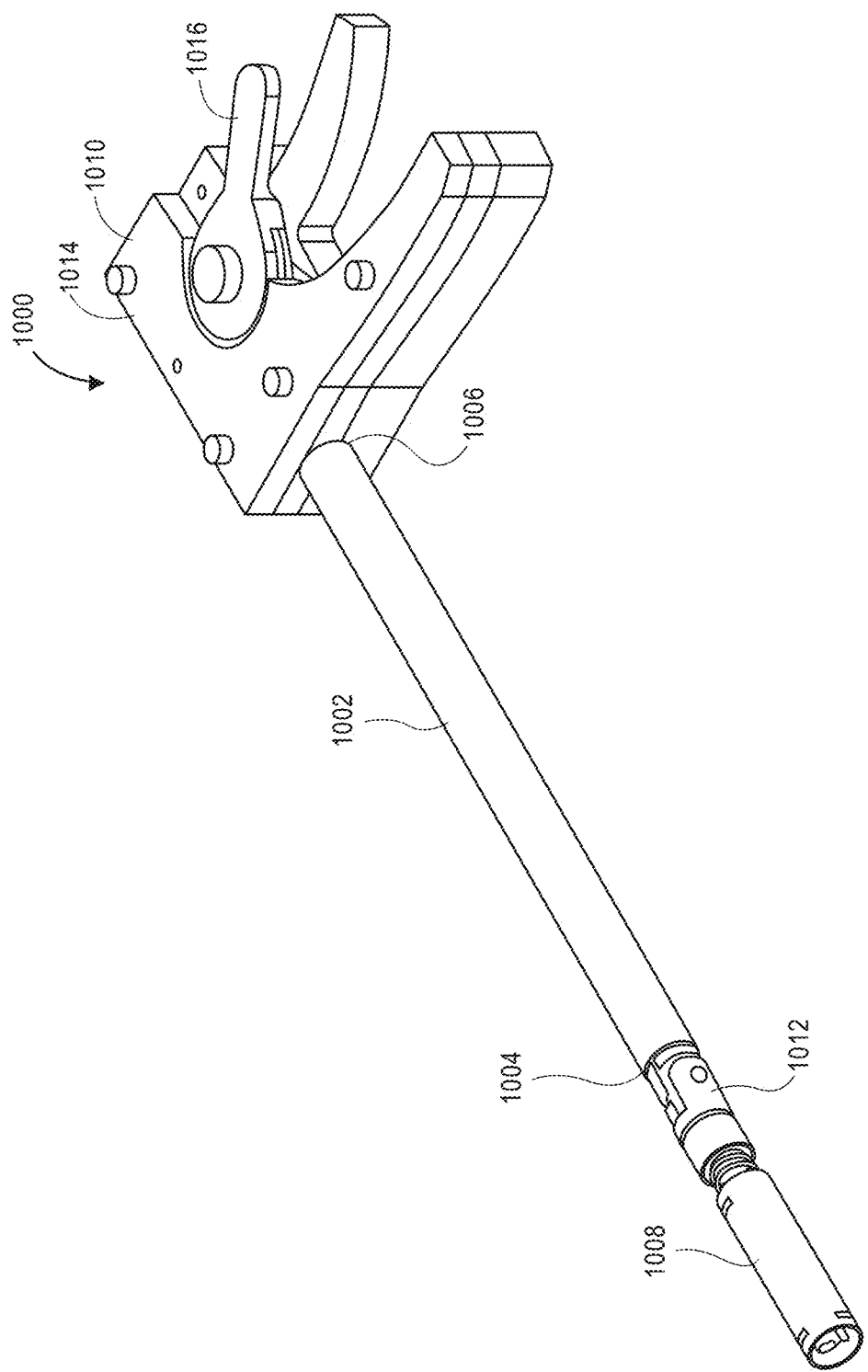
FIG. 10 is an isometric view of a surgical tool exchanger according to an example implementation of the present disclosure.
Figure 11:
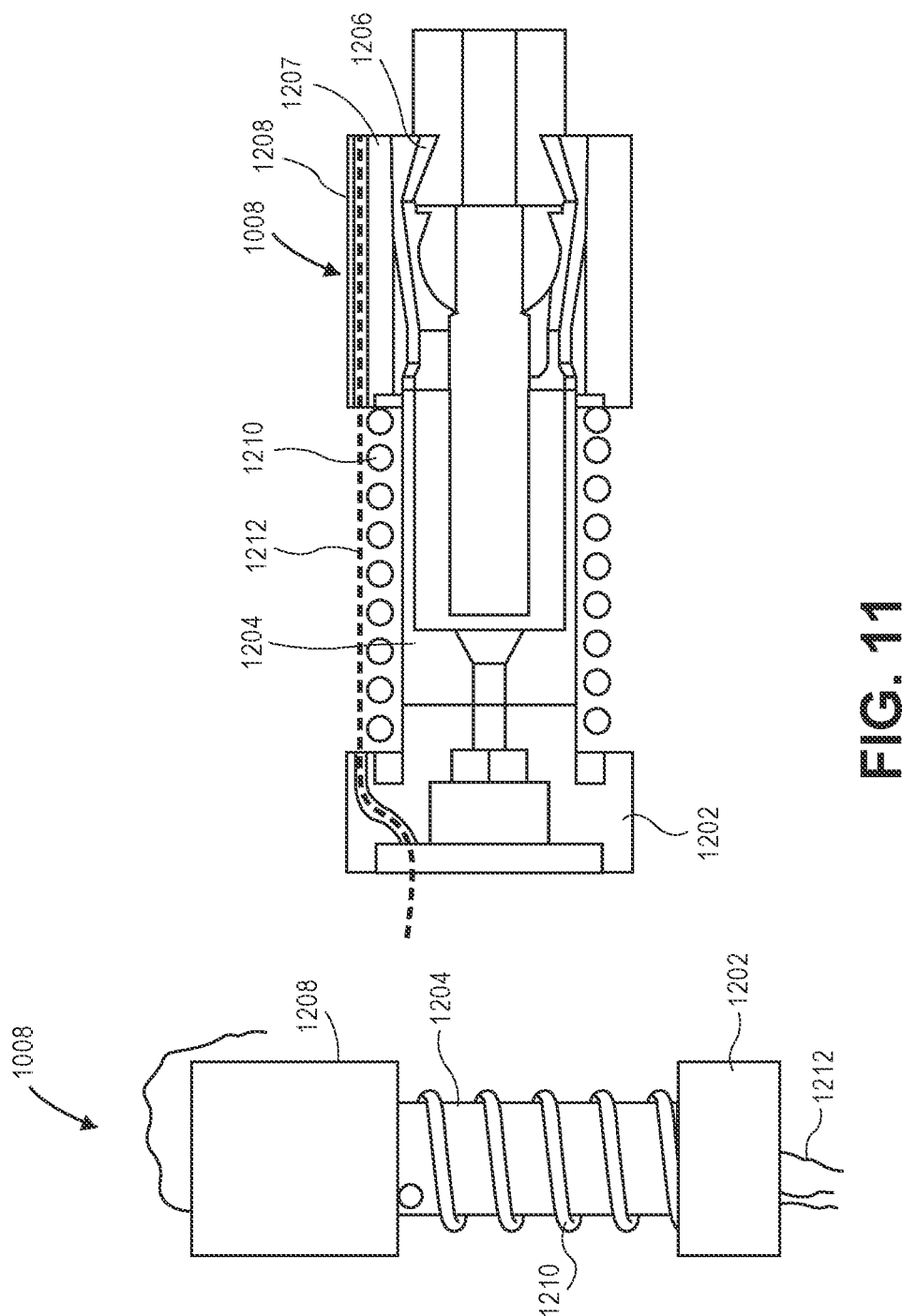
FIGS. 11 through 13C are side views of an end effector of the surgical tool exchanger according to example implementations of the present disclosure.
Figure 12:
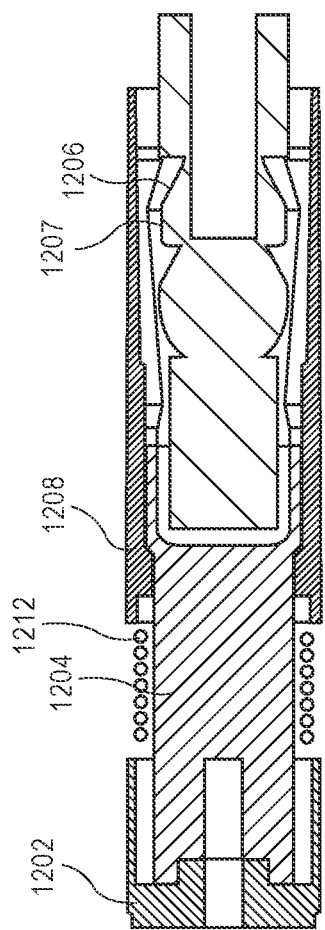

FIG. 10 illustrates another surgical tool exchanger 1000 according to another example implementation of the present disclosure. The surgical tool exchanger 1000 includes an elongated base 1002, or elongated shaft, having a first end 1004 and a second end 1006. The surgical tool exchanger 1000 also includes an end effector 1008 that is disposed proximate to the first end 1004 and an actuator 1010 connected to the second end 1006. The actuator 1010 can actuate the end effector 1008 to retain a removable surgical tool in a first actuation state and release the removable surgical tool in a second actuation state.

As shown in FIG. 10, the surgical tool exchanger 1000 also includes an elbow 1012. Additionally, the actuator 1010 may comprise a handle assembly 1014. The elbow 1012 can be operated similar to the elbow 1012 described above. For example, the surgical tool exchanger 1000 can include one or more elbow actuation cables that control movement of the elbow 1012. The handle assembly 1014 includes a wheel and lever mechanism 1016 that is connected to the elbow actuation cables. The operator can actuate the wheel and lever mechanism 1016 to control movement of the elbow 1012 via the elbow actuation cables.

FIGS. 11 through 13C illustrate an example end effector 1008 according to an example implementation. The end effector 1008 includes a base 1202, a body 1204 that is connected to the base 1202, jaws 1206 disposed within a grasping mechanism 1207, an overtube 1208, and a biasing member 1210. The base 1202 can be attached to the elbow 1012. For example, the base 1202 can be attached to one end of the elbow 1012 using a fastener, such as a screw or the like.

The body 1204 is attached to the base 1202 on one end and the jaws 1206 extend outwardly from the other side of the body 1204. In an implementation, the body 1204 can be attached to the base 1202 using a fastener so that the body 1204 is fixed with respect to the base 1202. In another implementation, the body 1204 can be received within an inner cavity defined within the base 1202. In an implementation, the jaws 1206 may be distinct from the body 1204 and may be attached to the body using fasteners or a suitable adhesive. For example, each jaw 1206 may be comprised of a steel beam having suitable materials disposed over the steel beam. In another implementation, the jaws 1206 may be integral with the body 1204 and formed through a suitable additive manufacturing process.

The overtube 1208 is received over the body 1204 and/or the jaws 1206 and can slide between a first position and a second position. An overtube actuator 1212 can exert a force on the overtube 1208 that causes the overtube 1208 to transition between the first position that biases the jaws 1206 in a grasping state and the second position that allows the jaws 1206 to transition to a non-grasping state. The overtube actuator 1212 may comprise a cable, string, or the like.

A biasing member 1210 is disposed about the body 1204 between the base 1202 and the overtube 1208. In an example implementation, the biasing member 1210 is a spring having a spring constant of at least 9.90 lbs/in (1.73 N/mm). The biasing member 1210 biases the overtube 1208 into the first position and can retract when the overtube 1208 exerts sufficient force against the biasing member 1210. For example, as the overtube actuator 1212 exerts a sufficient pulling force on the overtube 1208, the overtube 1208 causes the biasing member 1210 to retract to allow the overtube 1208 to transition to the second position. As the overtube 1208 transitions to the second position, the jaws 1206 deflect vertically, or expand, with respect to the body 1204 to enter a non-grasping state.

Once the pulling force is no longer sufficient, the biasing member 1210 exerts a force on the overtube 1208 causing the overtube 1208 to transition from the second position to the first position. As the overtube 1208 transitions from the second position to the first position, the overtube 1208 exerts a force on the grasping mechanism 1207 causing the jaws 1206 to contract. As the jaws 1206 contract, the jaws 1206 interface with corresponding barbs of the surgical tool. A portion of the overtube 1208 may extend passed an outside edge of the body 1204 so that the overtube 1208 interfaces with a surface of a robotic forearm. For example, the overtube 1208 may exert a force on a movable collet causing a decrease in friction between a grab ring and a portion of the surgical tool. Additionally, the movable collet can exert a pushing force against the overtube 1208, which causes the jaws 1206 to exert a pushing force against annular barbs the surgical tool.

Figure 13A:
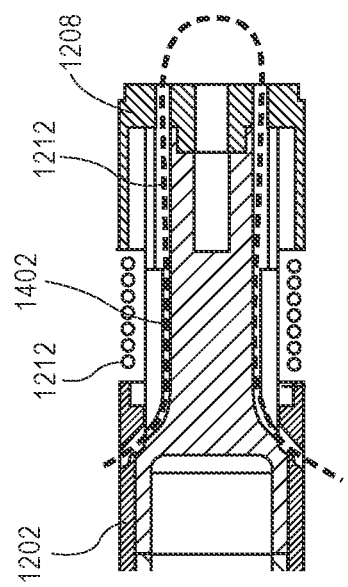
Figure 13B:
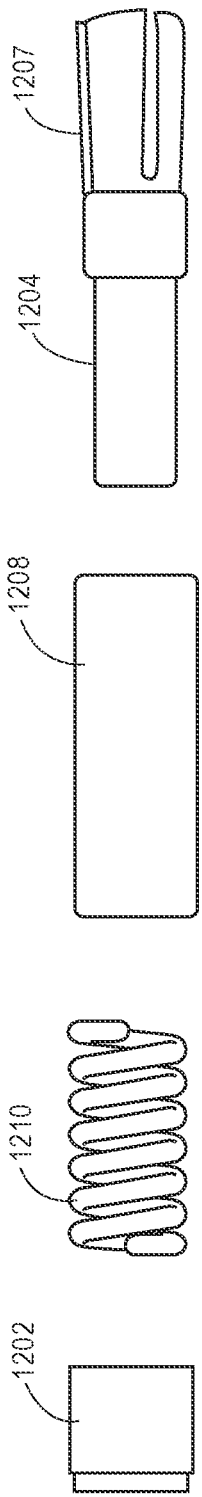
Figure 13C:
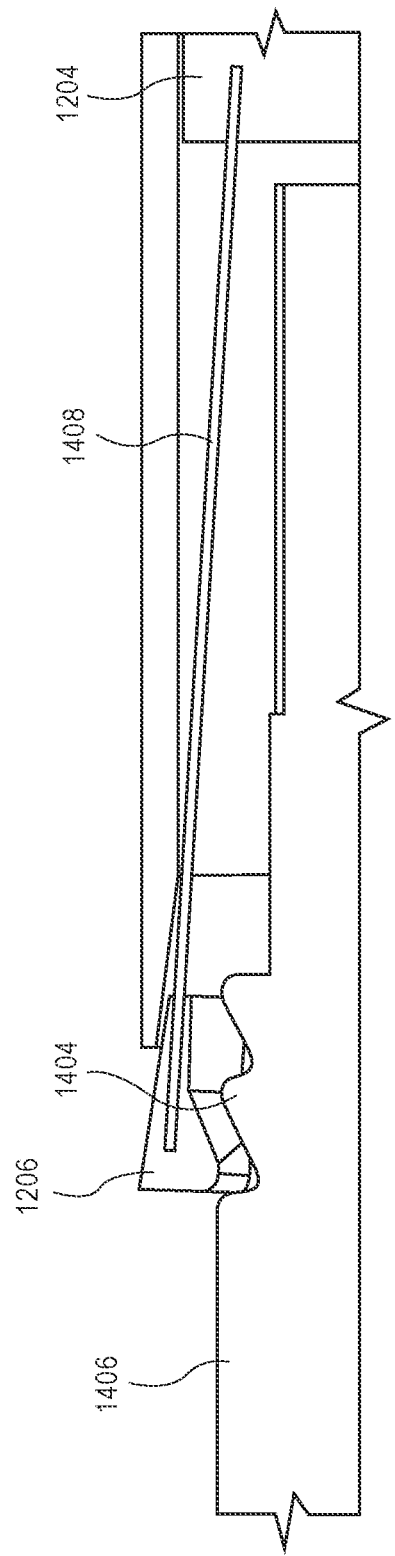

As shown in FIG. 13A, the body 1204 can define one or more channels 1402 that receive the overtube actuator 1212. For example, the channels 1402 may be formed within the body 1204 to receive a cable (the overtube actuator 1212). The cable is connected to the actuator 1010 at one end and the overtube 1208 at the other end. In some examples, the cables are disposed over the body 1204. FIG. 13C illustrates the jaws 1206 of the grasping mechanism 1207 interfacing with corresponding barbs 1404 of a surgical tool 1406. The jaws 1206 may be formed on a beam 1408. In an example implementation, the beam 1408 comprises spring steel.

Figure 14A:
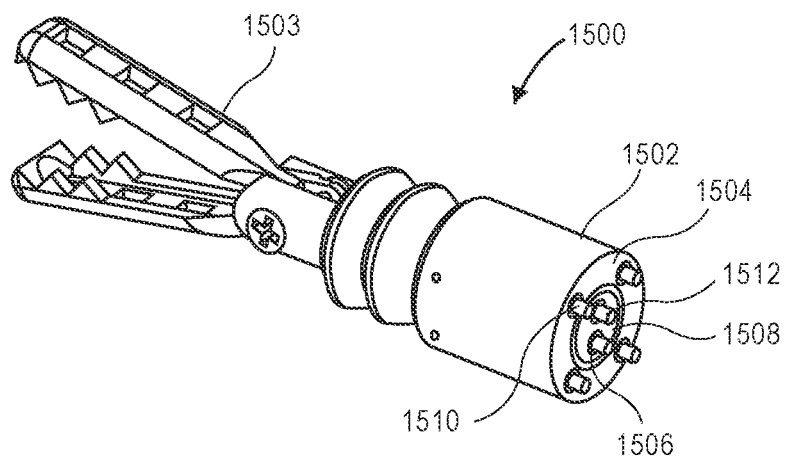
FIGS. 14A through 17F illustrate various surgical tools according to example implementations of the present disclosure.
Figure 14B:
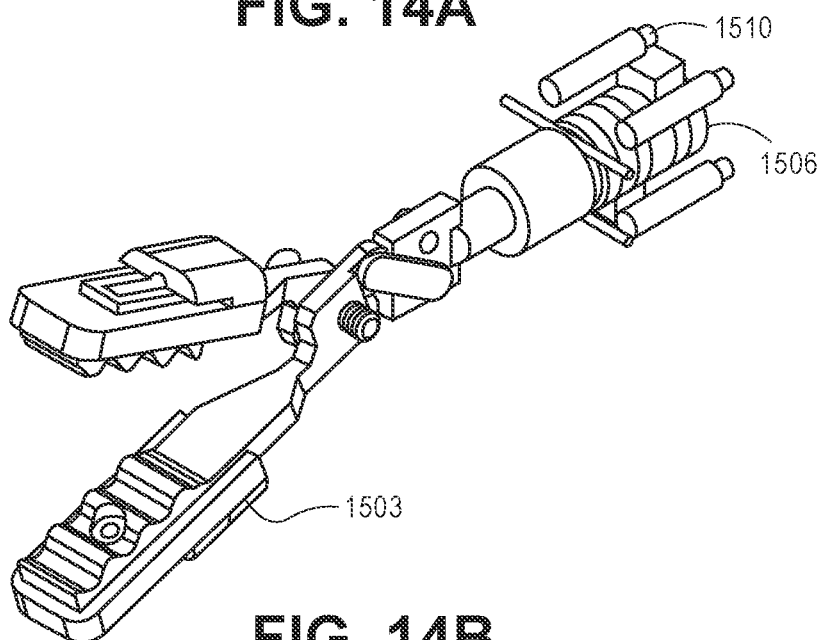
Figure 14C:
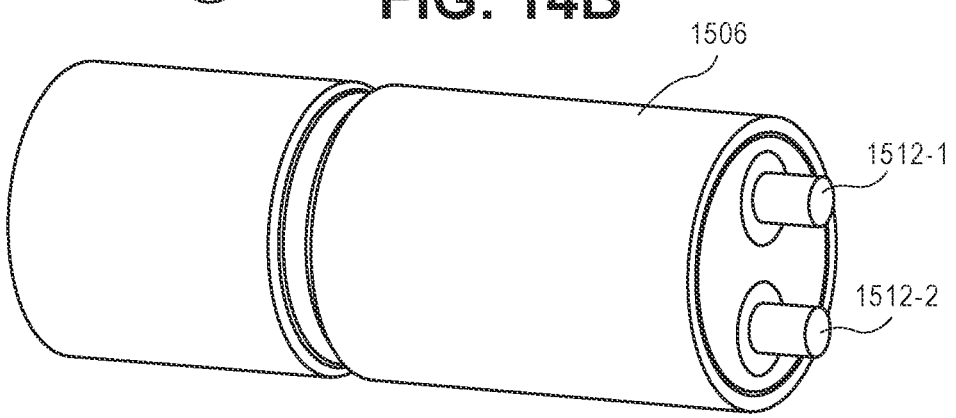

FIGS. 14A through 14C illustrate an example surgical tool 1500 according to an example implementation of the present disclosure. The surgical tool 1500 includes a housing 1502 and a tool 1503 connected to the housing 1502. In this implementation, the tool 1503 comprises a grasper. However, it is understood that other surgical tools can be used as well, as discussed below.

The housing 1502 includes a first face 1504 and an inner member 1506. The inner member 1506 can rotate within the housing 1502 about a central axis of the housing 1502. As shown, the surgical tool 1500 also includes a second face 1508. In an example implementation, the first face 1504 and the second face 1508 are coplanar and concentric. In some implementations, the second face 1508 is smaller than the first face 1504.

The surgical tool 1500 can be retained by a surgical robot. For example, the first face 1504 engages with a rotation face of the surgical robot, and the second face 1508 engages with an actuation face of the surgical robot. The rotation face can cause rotation of the first face 1504, and the actuation face causes rotation of the second face 1508. The first face 1504 and the second face 1508 can each include a plurality of pins 1510, 1512 that extend outwardly from the respective face 1504, 1508. The pins 1510, 1512 engage with respective pockets defined within the actuation face and/or the rotation face of the surgical robot.

In various implementations, the pins 1510, 1512 are spring-loaded brass alloyed gold plated spring pins. The pins 1510, 1512 serve to transfer rotation from the surgical robot to the surgical tool 1500 to cause actuation of the tool 1503. In some implementations, the pins 1512 that extend from the second face 1508 can electrically connect with the respective pocket of the surgical robot. In some examples, a first pin 1512-1 and a second pin 1512-2 of the pins 1512 electrically connect with the respective pockets and are electrically isolated from one another.

Figure 15:
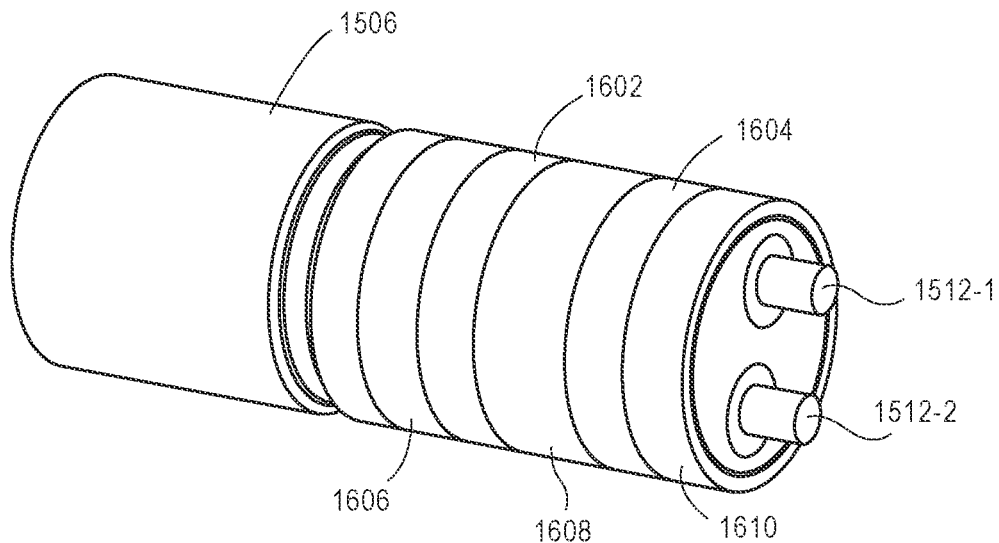

As shown in FIG. 15, the inner member 1506 includes conductive bands 1602, 1604 and insulator bands 1606, 1608, 1610 disposed between the conductive bands 1602, 1604. In some implementations, the conductive band 1602 is electrically connected to the first pin 1512-1, and the conductive band 1604 is electrically connected to the second pin 1512-2.

Figure 16:
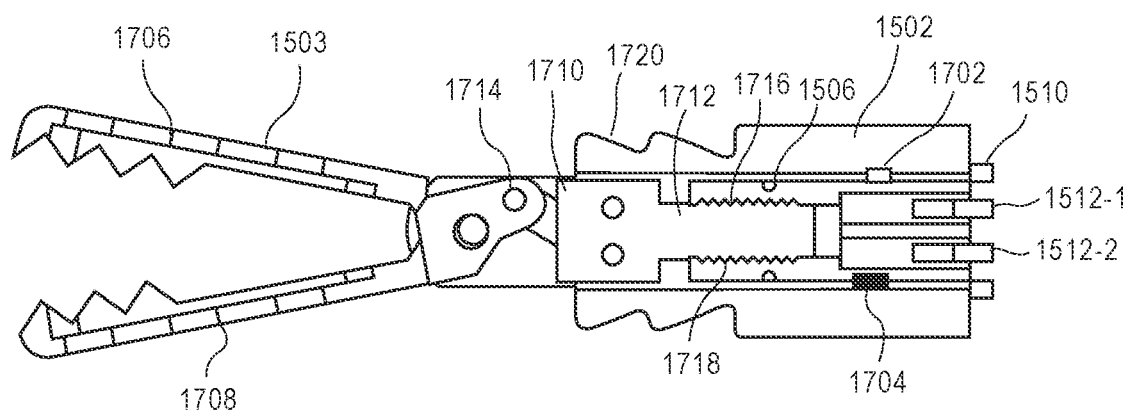
Figure 17A:
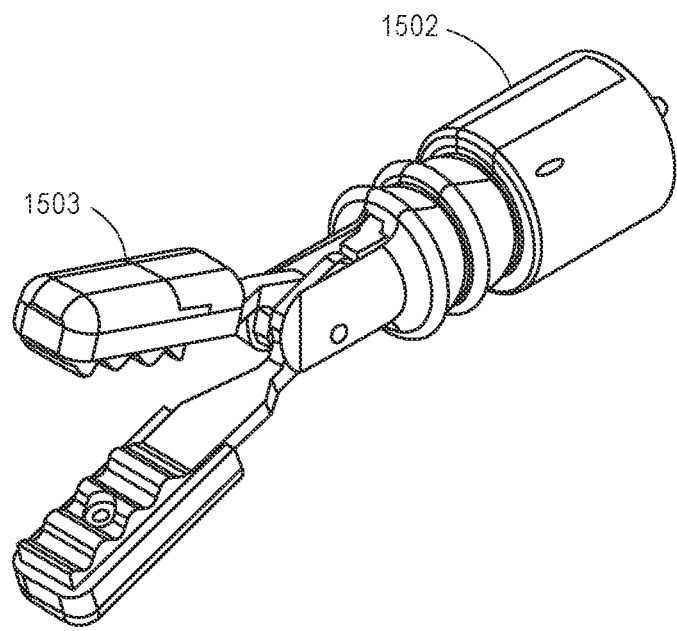
Figure 17B:
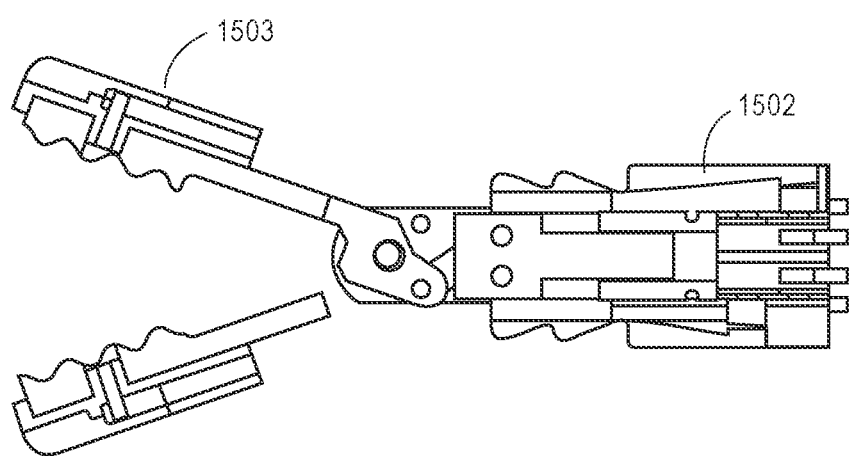
Figure 17C:
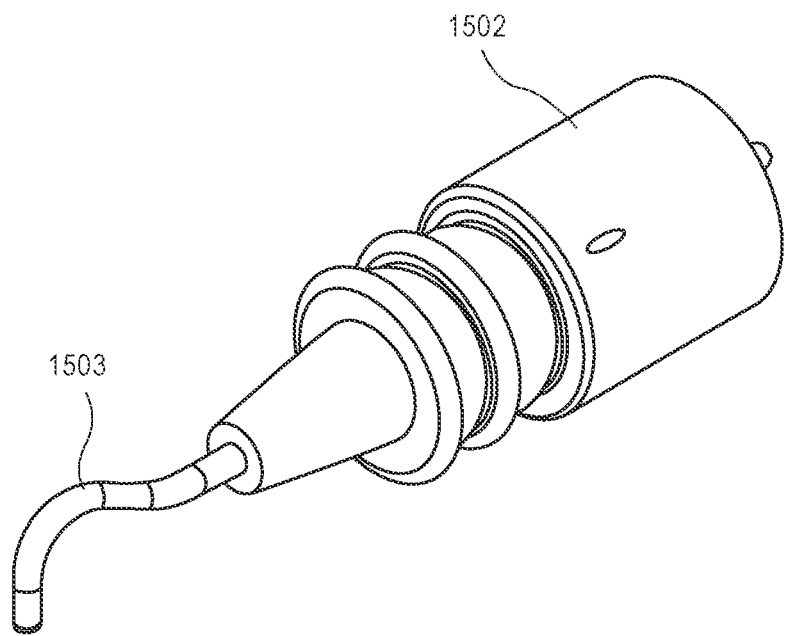
Figure 17D:
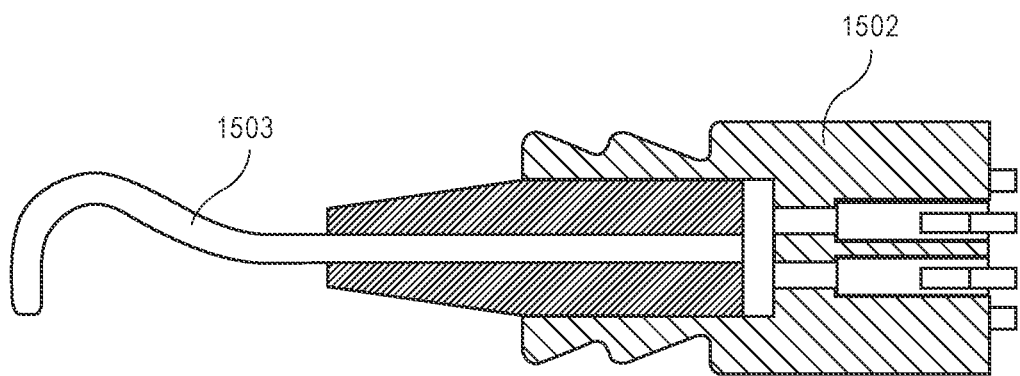
Figure 17E:
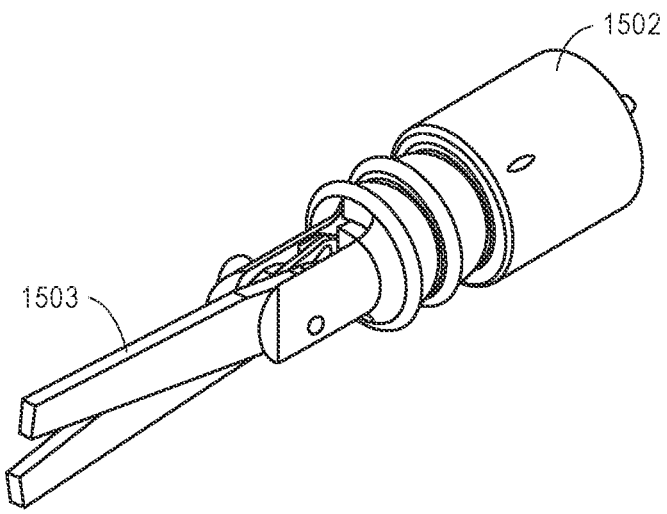
Figure 17F:
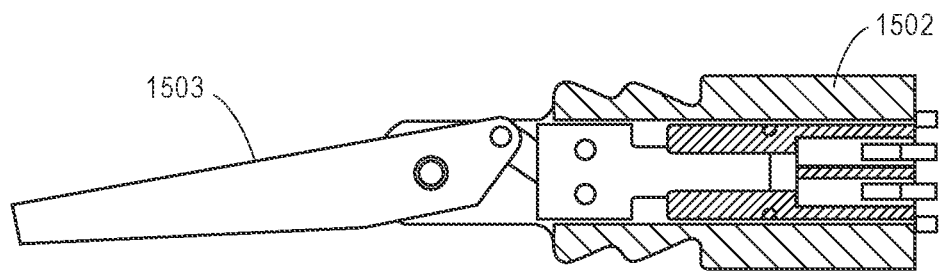

As shown in FIG. 16, the housing 1502 includes a first conductor 1702 that engages the conductive band 1602 at a first location and a second conductor 1704 that engages the conductive band 1604 at a second location. During operation, the first and second locations can change as the inner member 1506 rotates with respect to housing 1502.

The tool 1503 includes a first member 1706 and a second member 1708. The members 1706, 1708 are pivotally connected to the housing 1502. For example, the members 1706, 1708 are connected to a base 1710 that is fixed with respect to the housing 1502. For example, a fastener, such as a screw, can fix the base 1710 with the housing 1502.

The base 1710 is pivotally connected with a screw 1712 disposed within the housing 1502. The screw 1712 is also fixed with respect to the housing 1502 by the fastener. A joint 1714 connects the base 1806 with the screw 1712. A threaded member 1716 of the screw 1712 is connected to threads 1718 of the inner member 1506. The threaded member 1716 of the screw 1712 can slide along an axis parallel to the central axis. Since the screw 1712 is fixed with respect to the housing 1502, threaded member 1716 is prevented from rotating. As the pins 1512 rotate the inner member 1506 with respect to the housing 1502, the inner member 1506 exerts a force on the threated member 1716 of screw 1712, which causes the screw 1712 to slide horizontally. The screw 1712 causes the joint 1714 to pivot, which causes the members 1706, 1708 to pivot with respect to each other.

The housing 1502 can be configured in a variety of ways to interface with an end effector, such as the end effectors described above. For example, as shown in FIG. 16, the housing 1502 can include annular barbs 1720 that interface with an end effector. For example, the surgical tool 1500 can be mounted or unmounted from the surgical robot using surgical tool exchangers, such as the surgical tool exchanger 100 or surgical tool exchanger 1000 described above. The annular barbs 1720 are symmetric about the central axis of the housing 1502 and remain exposed when the surgical tool 1500 is held by the surgical robot to allow the end effector to engage with the surgical tool 1500. FIGS. 17A through 17F illustrate additional implementations of the surgical tools.

Figure 18:
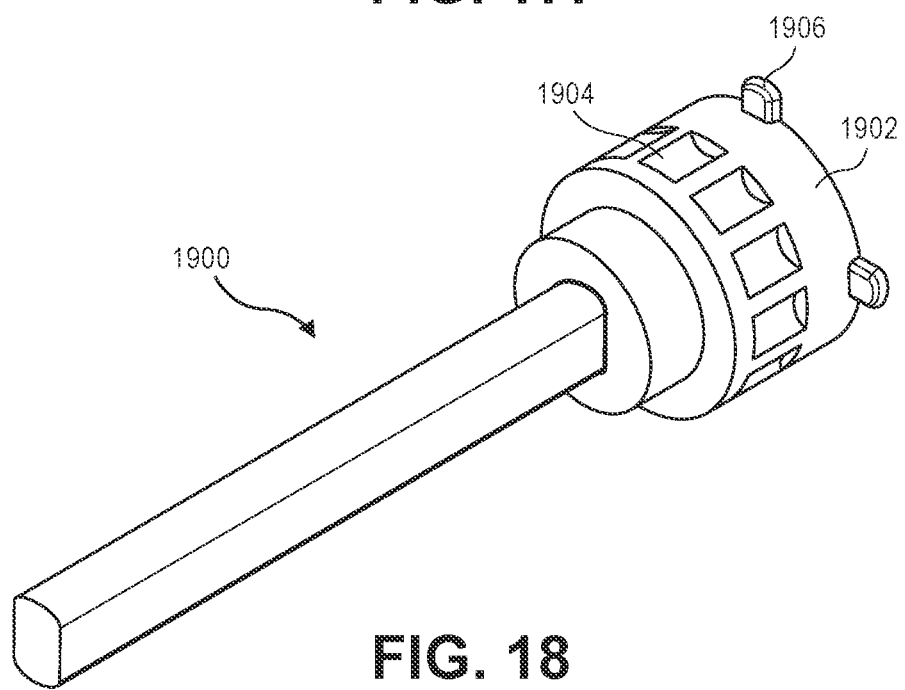
FIG. 18 illustrates another surgical tool according to an example implementation of the present disclosure.

As shown in FIG. 18, a surgical tool 1900 including a housing 1902 is illustrated. The housing 1902 includes elongated recesses 1904 that extend parallel to the central axis of the housing 1902 and remain exposed when the surgical tool 1900 is held by the surgical robot. The end effector of the surgical tool exchanger can engage with the elongated recesses 1904 for mounting or unmounting purposes. The housing 1902 may also include catch pins 1906 that extend perpendicular with respect to the central axis of the housing 1902. The catch pins 1906 interface with corresponding grooves of a surgical robot when the surgical tool 1900 is rotated. For example, during mounting, a surgical tool exchanger can rotate the surgical tool 1900 such that catch pins 1906 interface with corresponding grooves defined within a sleeve (e.g., robotic forearm) of the surgical robot allowing the surgical tool 1900 to be locked with respect to the sleeve.

Figure 19:
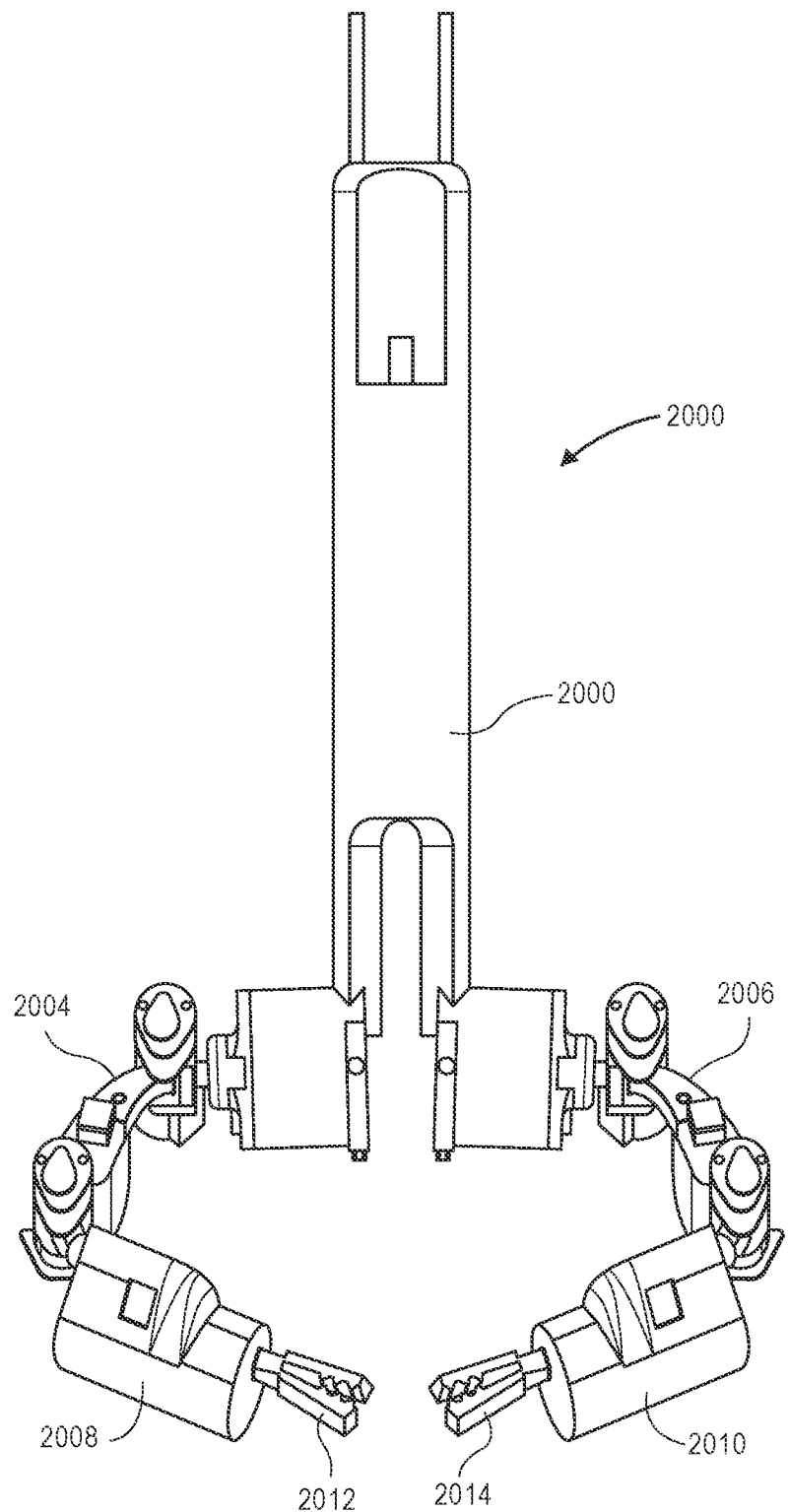
FIG. 19 illustrates an example surgical robot according to an example implementation of the present disclosure.

FIG. 19 illustrates an example surgical robot 2000 in accordance with an example implementation of the present disclosure. The surgical robot 2000 includes a body 2002, a first robotic arm 2004, and a second robotic arm 2006. The robotic arms 2004, 2006 each include respective robotic forearms 2008, 2010. The robotic forearms 2008, 2010 can receive surgical tools 2012, 2014 to allow the surgical robot 2000 to perform surgical operations. An example of a surgical robot is described, for example, in U.S. Patent Pub. No. 2017/0119482, which is incorporated herein by reference.

FIGS. 20A through 22 illustrate an example robotic arm 2100 in an example implementation of the present disclosure. The robotic arm 2100 includes a first rotary engagement mechanism 2102 that engages a housing of a surgical tool, such as the removable surgical tools described above, and selectively rotates the housing. The robotic arm 2100 also includes a second rotary engagement mechanism 2104 that engages an inner member of the surgical tool and can selectively rotate the inner member with respect to the housing.

The first rotary engagement mechanism 2102 includes a rotation face 2106, and the second rotary engagement mechanism 2104 includes an actuation face 2108. In some implementations, the rotation face 2106 is coplanar with the actuation face 2108. In some implementations, the rotary engagement mechanisms 2102, 2104 include gears, such as ring gears, directly coupled to the respective rotary engagement mechanisms 2102, 2104.

Figure 21:
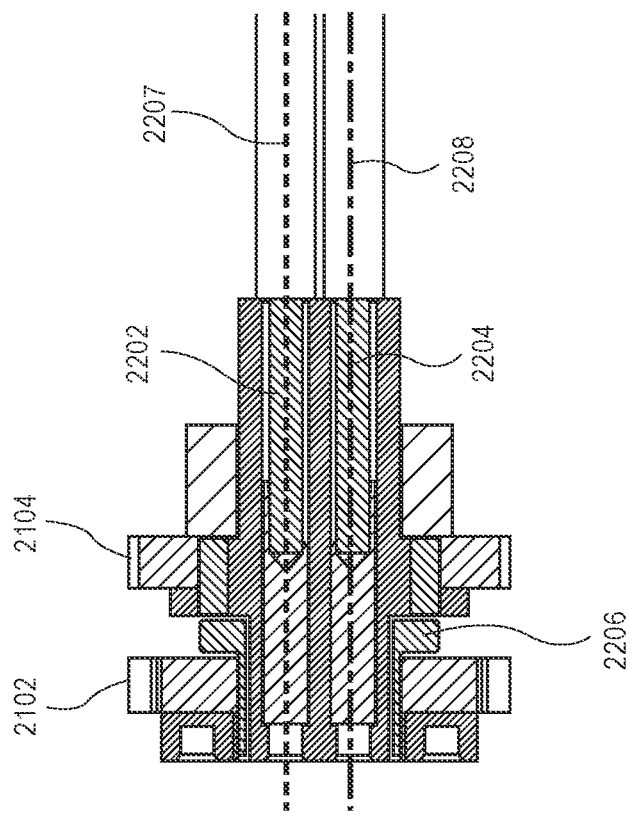
FIGS. 20A through 22 illustrate a robotic arm according to an example implementation of the present disclosure.

The rotation face 2106 and the actuation face 2108 each define multiple pockets 2110, 2112 that receive respective pins of the inner member and/or housing of the replaceable surgical tool. As shown in FIG. 21, the robotic arm 2100 includes contact pins 2202, 2204 that can provide an electrical connection to the pins of the inner member of the surgical tool. The contact pins 2202, 2204 can comprise a suitable conductive material. A sleeve 2206 is disposed between the first rotary engagement mechanism 2102 and the second rotary engagement mechanism 2104 to isolate rotational functionality. Electrical connections 2206, 2208 can supply power to the respective contact pins 2202, 2204. The electrical connections 2206, 2208 and the contact pins 2202, 2204 may be electrically isolated from one another.

Figure 20B:
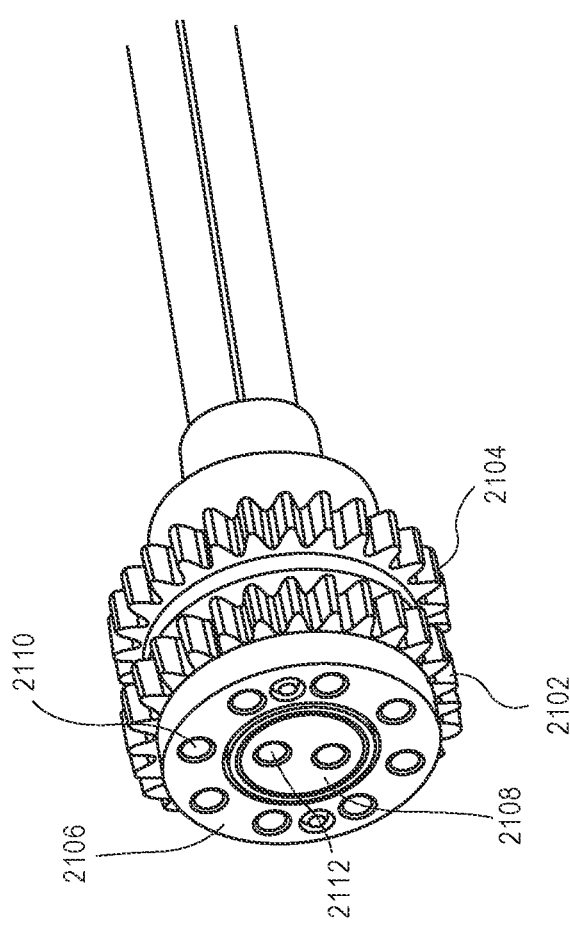

Referring to FIG. 20A, the robotic arm 2100 can include a first motor 2150 and a second motor 2152. The motors 2150, 2152 are connected to pinion gears 2154, 2156 that mesh with the rotary engagement mechanisms 2102, 2104. The motors 2150, 2152 selectively drives the pinion gears 2154, 2156 based upon instructions received by the surgical robot to operate the surgical tools. Thus, the pinion gear 2154 can operate the rotation face 2106 and the pinion gear 2156 can operate the actuation face 2108.

In some implementations, the motors 2150, 2152 are different motors. For example, the motor 2150 may rotate the actuation face 2108 faster with respect to the rotation face 2106 for purposes of operating the surgical tool. For example, the motor 2150 may be a Faulhaber 0620 C 006 B motor, and the motor 2152 may be a Faulhaber 0620 C 012 B motor. The robotic arm 2100 also includes a controller 2158 that controls operation of the motors 2150, 2152 based upon control signals received from the surgical robot.

Figure 22:
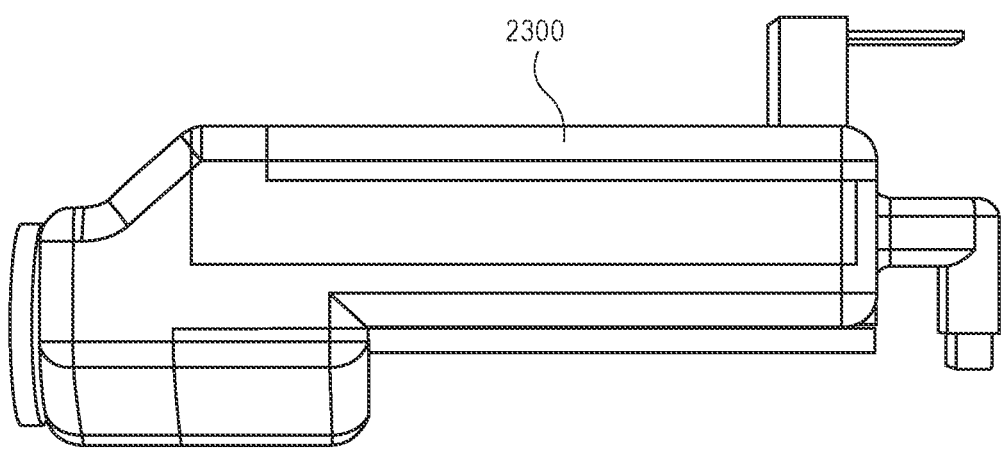

The robotic arm 2100 may also include a retention member 2160 that selectively presses an end of the surgical tool against the rotation face 2106 and the actuation face 2108. FIG. 22 illustrates an example housing 2300 for the robotic arm 2100.

Figure 23:
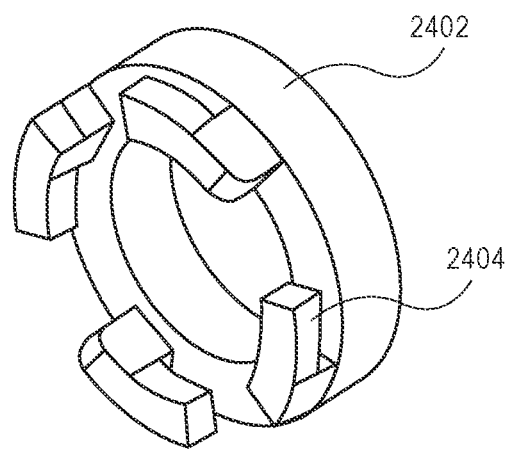
FIG. 23 illustrates an example retention member according to an example implementation of the present disclosure.

FIG. 23 illustrates an example retention member 2160 that comprises a body 2402 defining multiple grooves 2404 that receive a corresponding catch pin of the surgical tool providing twist-to-lock fitting functionality. For example, the grooves 2404 may receive a corresponding catch pin 1906 to maintain the surgical tool 1900 in position.

Figure 24A:
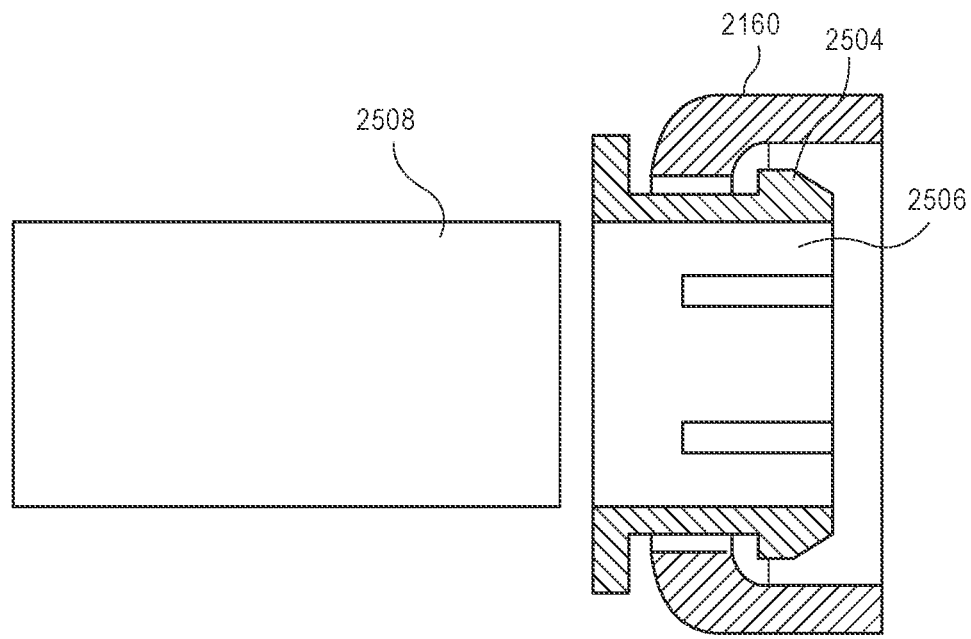
FIGS. 24A and 24B illustrate an example retention member according to an example implementation of the present disclosure.
Figure 24B:
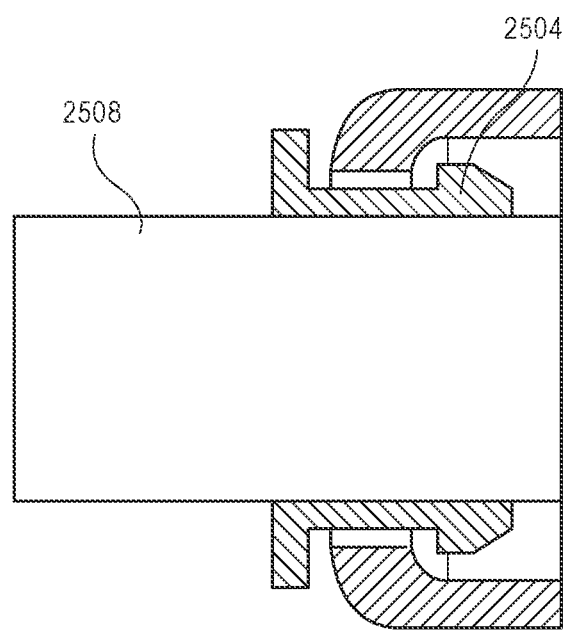

In some implementations, such as shown in FIGS. 24A and 24B, the retention member 2160 comprises a releasable push fitting. For instance, the retention member 2160 comprises a movable collet 2504 and a grab ring 2506. The grab ring 2506 can be disposed within the movable collet 2504, and the movable collet 2504 presses against the grab ring 2506 to grip a cylindrical portion 2508 of the surgical tool. An example of a movable collet and grab ring is described, for example, in U.S. Patent Pub. No. 2016/0327196, which is incorporated herein by reference.

Figure 25:
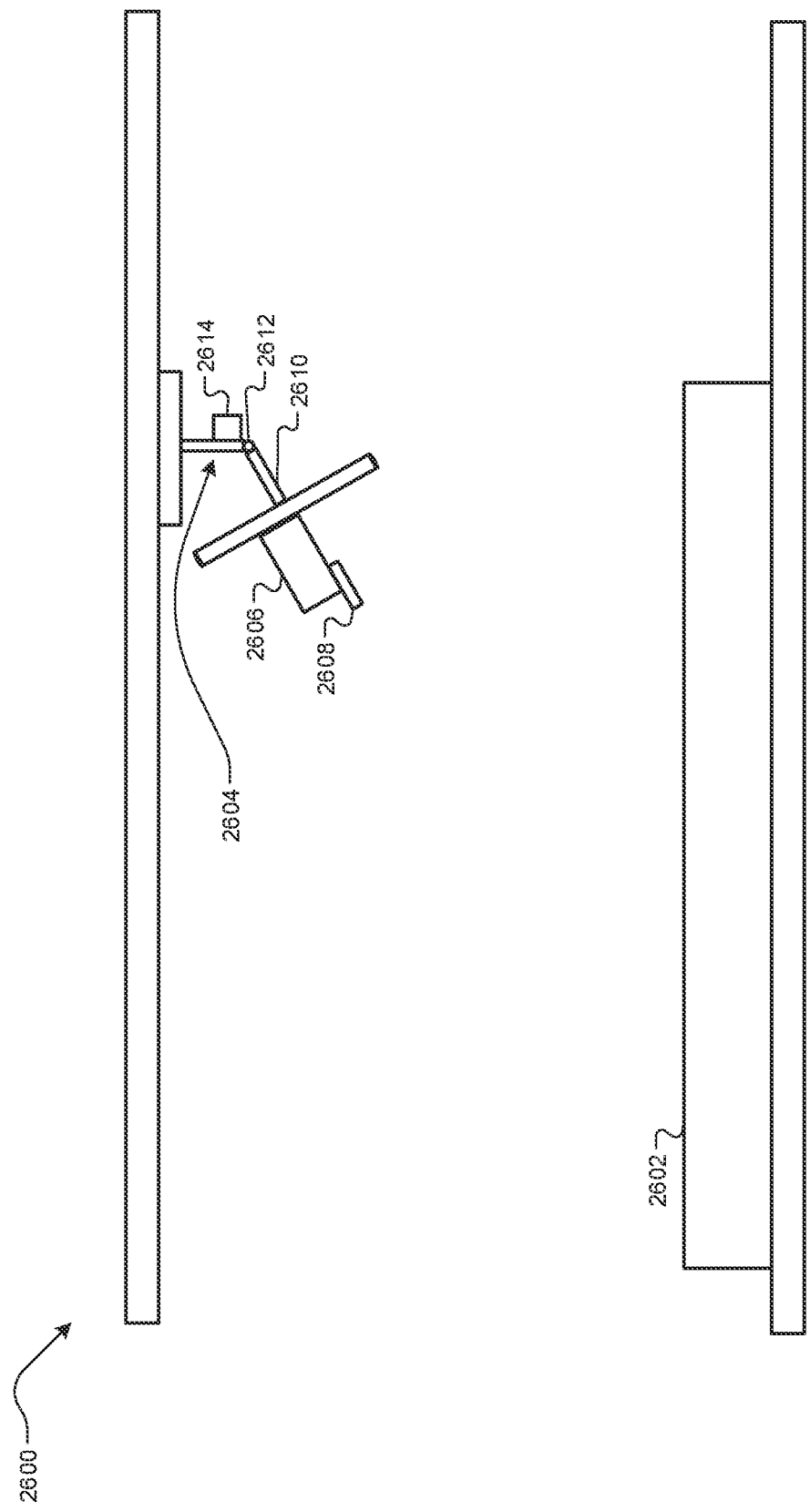
FIG. 25 illustrates an example medical environment according to an example implementation of the present disclosure.

FIG. 25 illustrates an example medical environment 2600 that includes an operating platform 2602, a support structure 2604, an image capture device 2606, and an electromagnetic radiation source 2608. The image capture device 2606 and the electromagnetic radiation source 2608 are connected to the support structure 2604, and the support structure 2604 can be attached to any suitable structure within the medical environment 2600. For example, the support structure 2604 may be attached to a roof or a wall.

The image capture device 2606 captures images within a field-of-view of the image capture device 2606. The images may be still images, video, or the like. The electromagnetic radiation source 2608 may be a laser pointer. For example, the electromagnetic radiation source 2608 may be laser diode that emits a coherent beam of visible light that can be used to highlight a point of interest.

The support structure 2604 can include one or more arms 2610 connected to one or more hinges 2612 that allow the support structure 2604 to be repositioned to change the field-of-view of the image capture device 2606 and/or highlight another point of interest using the electromagnetic radiation source 2608. The one or more arms 2610 support the image capture device 2606 and/or the electromagnetic radiation source 2608. The support structure 2604 can include an actuator 2614 that is configured to actuate the one or more arms 2610. The actuator 2614 may be controlled by one or more electronic signals.

Figure 26:
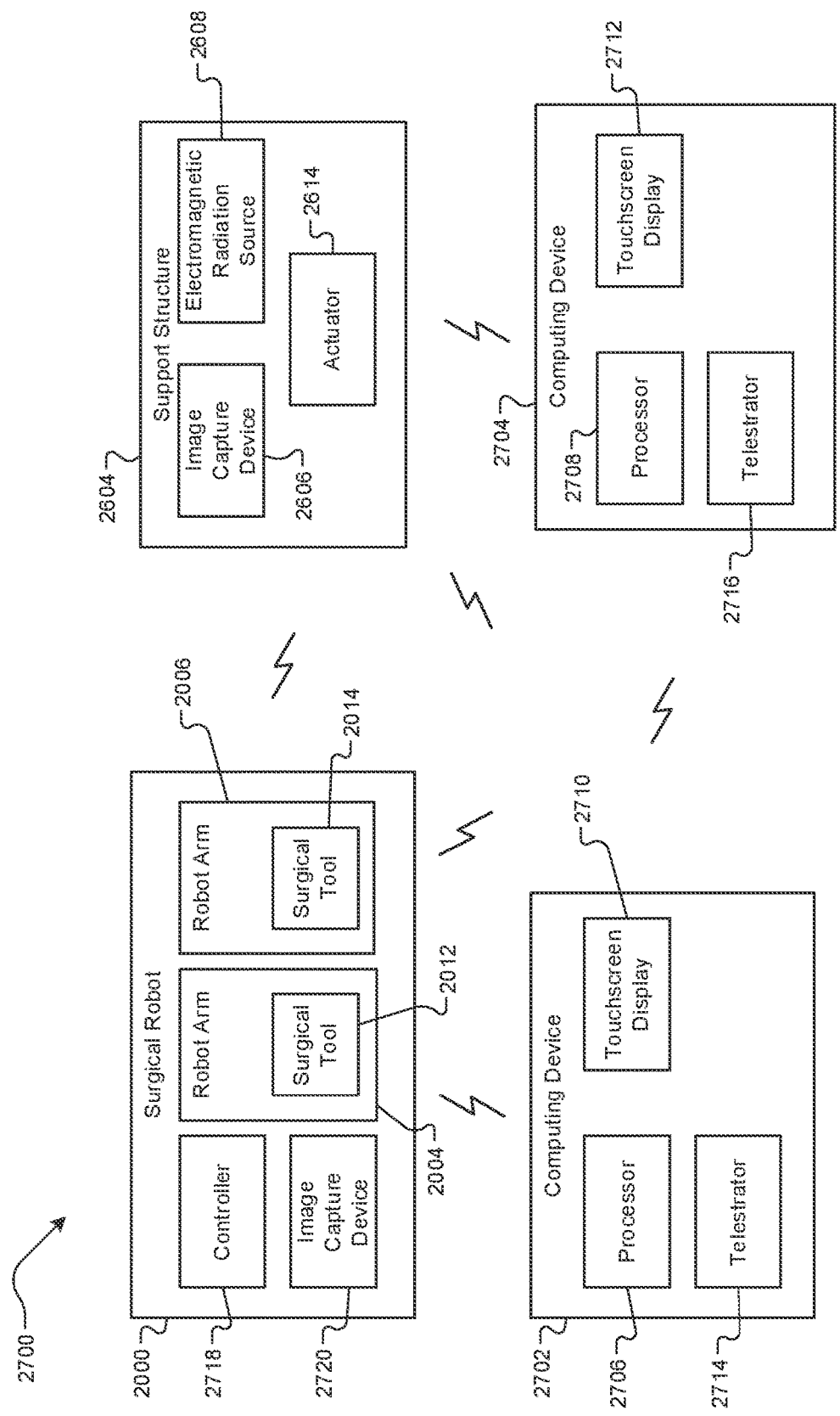
FIG. 26 illustrates an example communication system used within the example medical environment according to an example implementation of the present disclosure.

FIG. 26 illustrates an example communication system 2700 according to an example implementation of the present disclosure. The communication system 2700 can comprise a wired communication system or a wireless communication system. The communication system 2700 includes the surgical robot 2000, a computing device 2702, a computing device 2704, and the support structure 2604. The computing devices 2702, 2704 include respective processors 2706, 2708, respective touchscreen displays 2710, 2712, and respective telestrators 2714, 2716. The surgical robot 2000 includes a controller 2718, an image capture device 2720, robotic arms 2004, 2006, and surgical tools 2012, 2014.

The communication system 2700 allows medical personnel within a medical environment to communicate with other medical personnel at another location. For example, the medical personnel may communicate with one another through the computing devices 2702, 2704. Additionally, images captured by the image capture devices 2606, 2720 may be displayed by the touchscreen displays 2710, 2712. Medical personnel can also use the telestrators 2714, 2716 to visually indicate areas of interest, which can be broadcast to other displays. For example, visual indicators captured at a first telestrator can be generated at a second telestrator for collaboration purposes.

Medical personnel can also reposition the support structure 2604 by controlling the actuator 2614 via the computing devices 2702, 2704. Thus, the support structure 2604 can be manipulated to reposition the image capture device 2606 and/or the electromagnetic radiation source 2608. Thus, remote medical personnel can change the field-of-view of the image capture device 2606 or change the position of the electromagnetic radiation source 2608 to identify a new area of interest. In some implementations, the surgical robot 2000 can be controlled by medical personnel via the computing devices 2702, 2704, which provides medical personnel at different locations the ability to manipulate the surgical robot 2000 during a medical procedure.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A surgical tool exchanger comprising:
an elongated base having a first end and a second end;
an end effector configured to receive a replaceable surgical tool and comprising:
  a body;
  a plurality of jaws;
  a first beam holding a first jaw of the plurality of jaws and extending outwardly from the body;
  a second beam holding a second jaw of the plurality of jaws and extending outwardly from the body;
  a first intermediate portion disposed on the first beam between the first jaw and the body;
  a second intermediate portion disposed on the second beam between the second jaw and the body;
  a slider configured to slide within a cavity defined in the body between a first position and a second position;
  a first end effector actuator directly connected to the second jaw and the slider and passing through the first intermediate portion;
  a second end effector actuator directly connected to the first jaw and the slider and passing through the second intermediate portion;
an elbow configured to allow the end effector to pivot with respect to the elongated base; and
a main actuator connected to the second end of the elongated base and operatively connected to the end effector and configured to cause the end effector to retain the replaceable surgical tool in a first actuation state and release the replaceable surgical tool in a second actuation state.

2. The surgical tool exchanger of claim 1, wherein in the first actuation state, the main actuator causes the plurality of jaws to grip the replaceable surgical tool, and
wherein in the second actuation state, the main actuator causes the plurality of jaws to release the replaceable surgical tool.

3. The surgical tool exchanger of claim 2, wherein, in the first actuation state, the main actuator causes the slider to move to the first position, and
wherein, in the second actuation state, the main actuator causes the slider to move to the second position.

4. The surgical tool exchanger of claim 3, wherein:
the first end effector actuator includes a first cable configured to be pulled by the slider; and
the second end effector actuator includes a second cable configured to be pulled by the slider.

5. The surgical tool exchanger of claim 3, wherein the first end effector actuator and the second end effector actuator are arranged in a crisscross configuration.

6. The surgical tool exchanger of claim 1, further comprising:
a first rod within the elongated base;
a second rod within the end effector; and
a joint located within the elbow, wherein the joint transfers rotational motion of the first rod to the second rod.

7. A surgical tool exchanger comprising:
an elongated base having a first end and a second end;
an end effector connected to the elongated base configured to receive a replaceable surgical tool;
a main actuator connected to the second end of the elongated base and operatively connected to the end effector and configured to cause the end effector to retain the replaceable surgical tool in a first actuation state and release the replaceable surgical tool in a second actuation state,
wherein the end effector comprises:
a body;
a plurality of jaws connected to the body, wherein
in the first actuation state, the main actuator causes the plurality of jaws to grip the replaceable surgical tool, and
in the second actuation state, the main actuator causes the plurality of jaws to release the replaceable surgical tool;
a first beam holding a first jaw of the plurality of jaws and extending outwardly from the body;
a second beam holding a second jaw of the plurality of jaws and extending outwardly from the body;
a first intermediate portion disposed on the first beam between the first jaw and the body;
a second intermediate portion disposed on the second beam between the second jaw and the body;
a slider configured to slide within a cavity defined in the body between a first position and a second position;
a first end effector actuator directly connected to the second jaw and the slider and passing through the first intermediate portion; and
a second end effector actuator directly connected to the first jaw and the slider and passing through the second intermediate portion, wherein:
in the first actuation state, the main actuator causes the slider to move to the first position, and
in the second actuation state, the main actuator causes the slider to move to the second position.

\* \* \* \* \*